US011807846B2

(12) United States Patent
Chen et al.

(10) Patent No.: US 11,807,846 B2
(45) Date of Patent: *Nov. 7, 2023

(54) METHODS FOR TRANSFORMING CORN EXPLANTS

(75) Inventors: Yurong Chen, Verona, WI (US); Brian J. Martinell, Mt. Horeb, WI (US); Anatoly Rivlin, Brooklyn, WI (US); Yuechun Wan, Madison, WI (US); Edward J. Williams, Madison, WI (US); Xudong Ye, Madison, WI (US); Ashok Shrawat, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/873,092

(22) Filed: Apr. 29, 2012

(65) Prior Publication Data
US 2022/0340925 A1 Oct. 27, 2022

Related U.S. Application Data

(60) Provisional application No. 61/639,992, filed on Apr. 29, 2012.

(51) Int. Cl.
C12N 15/00 (2006.01)
C12N 15/82 (2006.01)

(52) U.S. Cl.
CPC ..... *C12N 15/8275* (2013.01); *C12N 15/8274* (2013.01)

(58) Field of Classification Search
CPC ............ C12N 15/8201; C12N 15/8209; C12N 15/8271; C12N 5/04; C12N 15/8275
See application file for complete search history.

(56) References Cited

U.S. PATENT DOCUMENTS

| | | | |
|---|---|---|---|
| 6,995,016 B2 * | 2/2006 | Eudes | A01H 4/008 435/430.1 |
| 7,524,522 B2 | 4/2009 | DeLine et al. | |
| 7,938,345 B2 | 5/2011 | Teeter, Jr. et al. | |
| 11,713,465 B2 | 8/2023 | Duncan et al. | |
| 2005/0005321 A1 | 1/2005 | Martinell et al. | |
| 2008/0124727 A1 * | 5/2008 | Rout | A01H 4/001 435/6.15 |
| 2008/0280361 A1 * | 11/2008 | Calabotta et al. | 435/430 |
| 2009/0138985 A1 * | 5/2009 | Martinell et al. | 800/278 |
| 2022/0340916 A1 | 10/2022 | Duncan et al. | |

FOREIGN PATENT DOCUMENTS

| | | | | |
|---|---|---|---|---|
| EP | 1521840 B1 * | 4/2005 | ............ | C12N 15/87 |
| WO | WO 2003/0017752 | 3/2003 | | |

OTHER PUBLICATIONS

Li et al. 2002. Developmental, tissue culture, and genotypic factors affecting plat regeneration from shoot apical meristems of genrminated *Sea mays* L. seedlings. In Vitro cell. Dev. Biology-Plant 38: 285-292.*
Raven et al. 2005. Biology of Plants. Macmillan. p. 503.*
Ishida et al. 2007. Agrobacterium-mediated transformation of maize. Nature Protocols 2: 1614-1621. (Year: 2007).*
Hiei et al 2006. Improved frequency of transformation in rice and maize by treatment of immature embryos with centrifugation and heat prior to infection with Agrobacterium tumefaciens. Plant Cell Tiss Organ Cult 87: 233-243. (Year: 2006).*
Karami. 2008. Factors Affecting Agrobacterium-mediated transformation of Plants. Trangenic Plant Journal 2(2): 127-137. (Year: 2008).*
Bochardt et al. 1992. DNA Methylation is Involved in Maintenance of an Unusual Expression Pattern of an Introduced Gene. Plant Physiol 99: 409-414. (Year: 1992).*
U.S. Appl. No. 14/550,694, filed Nov. 21, 2014, Duncan et al.
Chai et al., "Optimum moisture contents of seeds stored at ambient temperatures," *Seed Science Research* 8:23-28, 1998.
Johnston et al., "Mass Isolation of Viable Wheat Embryos," *Nature* 179:160-161, 1957.
Senaratna et al., "Dehydration Injury in Germinating Soybean (*Glycine max* L. Merr.) Seeds," *Plant Physiol.* 72:620-624, 1983.
Vertucci et al., "Theoretical Basis of Protocols for Seed Storage," *Plant Physiol.* 94:1019-1023, 1990.
Jia et al., "Efficient maize (*Zea mays* L.) regeneration derived from mature embryos in vitro," *Maydica* 53; 239-248; 2008.
Esteves; Plant regeneration from mature embryos of maize (*Zea mays* L.); *Agriscientia* vol. XI; 79-82; 1994.
Abdelnour-Esquivel et al., "Cryopreservation of Zygotic Embryos of *Coffea* ssp.," Cryo-Letters 13:297-302, 1992.
Cho et al., "Transformation of recalcitrant barley cultivars through improvement of regenerability and decreased albinism," *Plant Science* 138:229-244, 1998.
Cho et al., "High-frequency transformation of oat via microprojectile bombardment of seed-derived highly regenerative cultures," *Plant Science* 148:9-17, 1999.
Cho et al., "Production of transgenic tall fescue and red fescue plants by particle bombardment of mature seed-derived highly regenerative tissues," *Plant Cell Reports* 19:1084-1089, 2000.
Cho et al., "Transformed $T_0$ orchardgrass (*Dactylis glomerata* L.) plants produced from highly regenerative tissues derived from mature seeds," *Plant Cell Reports* 20:318-324, 2001.
Cho et al., "Stable transformation of rice (*Oryza sativa* L.) via microprojectile bombardment of highly regenerative, green tissues derived from mature seed," *Plant Cell Reports* 22:483-489, 2004.

(Continued)

*Primary Examiner* — Karen M Redden
(74) *Attorney, Agent, or Firm* — Dentons US LLP; Paula DeGrandis

(57) ABSTRACT

The present invention provides methods for the production of viable explants from mature corn seeds, wherein the explant comprises the apical portion of the embryo axis of the corn seed. The present invention also relates to methods for producing such explants and for transforming the explants with a heterologous DNA.

35 Claims, 6 Drawing Sheets

(56) References Cited

OTHER PUBLICATIONS

Ha et al., "Stable Transformation of a Recalcitrant Kentucky Bluegrass (*Poa pratensis* L.) Cultivar Using Mature Seed-Derived Highly Regenerative Tissues," *In Vitro Cell. Dev. Biol.—Plant* 37:6-11, 2001.
Higley et al., "Effects of non-destructive tissue extraction on the viability of corn, soybean, and bean seeds," *Seed Sci. & Technol.* 22:245-252, 1994.
Li et al., "The Level of Expression of Thioredoxin is Linked to Fundamental Properties and Applications of Wheat Seeds," *Molecular Plant* 2:430-441, 2009.
Zhang et al., "Transformation of recalcitrant maize elite inbreds using in vitro shoot meristematic cultures induced from germinated seedlings," *Plant Cell Reports* 21:263-270, 2002.
Poehlman, J.M. 1987. Breeding field crops, 3rd ed. Van Nostram Reinhold Publisher. p. 39. (Year: 1987).
Vertucci et al., "Oxidative Processes in Soybean and Pea Seeds," Plant Physiol. 84:1038-1043, 1987.
Borisjuk et al., "The oxygen status of the developing seed," New Phytologist 182:17-30, 2009.
USPTO: Final Office Action regarding U.S. Appl. No. 14/550,694, dated Nov. 7, 2022.
USPTO: Response to Final Office Action regarding U.S. Appl. No. 14/550,694, filed Jan. 30, 2023.
Al-Abed et al., "Split-seed: a new tool for maize researchers," *Planta* 223:1355-1360, 2006.
Gordon-Kamm et al., "Transformation of maize cells and regeneration of fertile transgenic plants," *Plant Cell* 2:603-618, 1990.
Gould et al., "Transformation of *Zea mays* L. using *Agrobacterium tumefaciens* and the shoot apex," *Journal of Plant Physiology* 95:426-434, 1991.
Horn et al., "Use of HI II-Elite inbreds in Agrobacterium-based transformation of maize," *In Vitro Cellular & Developmental Biology—Plant* 42:359-366, 2006.
Huang et al., "High frequency plant regeneration through callus initiation from mature embryos of maize (*Zea mays* L.)," *Plant Cell Reports* 22:793-800, 2004.
Ishida et al., "High efficiency transformation of maize (*Zea mays* L.) mediated by *Agrobacterium tumefaciens*," *Nature Biotechnology* 14:745-750, 1996.
Li et al., "Developmental, tissue culture and genotypic factors affecting plant regeneration from shoot apical meristems of germinating *Zea mays* L. seedlings," *In Vitro Cellular & Developmental Biology—Plant* 38:285-292, 2002.
Sairam et al., "Shoot meristem: an ideal explants for *Zea mays* L. transformation," *Genome* 46:323-329, 2003.
Sidorov et al., "Agrobacterium mediated transformation of seedling-derived maize callus," *Plant Cell Reports* 25:320-328, 2006.
Songstad et al., "Production of transgenic maize plants and progeny by bombardment of Hi-II immature embryos," *In Vitro Cellular & Developmental Biology—Plant* 32:179-183, 1996.
Sticklen et al., "Shoot apical meristem: A sustainable explants for genetic transformation of cereal crops," *In Vitro Cellular & Developmental Biology—Plant* 41:187-200, 2005.
Wang et al., "Callus induction and plant regeneration from maize mature embryos," *Plant Cell Reports* 6:360-362, 1987.
Zhang et al., "Transformation of recalcitrant maize inbreds using in vitro shoot meristematic cultures induced from germinated seedlings," *Plant Cell Reports* 21:263-270, 2002.
Zhong et al., "In vitro morphogenesis of corn (*Zea mays* L.). I. Differentiation of multiple shoot clumps and somatic embryos from shoot tip," *Planta* 187:483-489, 1992.
Zhong et al., "The competence of maize shoot meristems for integrative transformation and inherited expression of transgenes," *Plant Physiology* 110:1097-1107, 1996.
Parmar et al., Plant regeneration from mature embryo of commercial Indian bread wheat (*Triticum aestivum* L.) cultivars, Physiol. Mol. Biol. Plants 18: 177-183, 2012.
The Seed Biology Place: Gerhard Leubner Lab of the University of London (http://www.seedbiology.de/structure.asp), accessed Jun. 14, 2015.

* cited by examiner

METHODS FOR TRANSFORMING CORN EXPLANTS

This application claims the priority of U.S. Provisional Patent Application Ser. No. 61/639,992, filed Apr. 29, 2012, the entire disclosure of which is specifically incorporated herein by reference.

BACKGROUND OF THE INVENTION

1. Field of the Invention

The invention relates to corn seed explants and related methods.

2. Description of Related Art

Corn (*Zea mays*) is an important crop and is a primary food source in many areas of the world. Biotechnological techniques have been used to significantly improve corn and other crop species in a number of agronomic and food quality traits. Development of transgenic crops in particular requires plant explant materials capable of being genetically transformed and regenerated into a transgenic plant capable of passing a transgene to progeny.

SUMMARY OF THE INVENTION

In one aspect, the invention provides a purified population of dry mature corn seed explants competent for genetic transformation, wherein the explants are comprised of the apical portion of the embryo axis of the seed lacking the radical; wherein remaining portions of the corn seed have been substantially removed from the explants. In one embodiment, the embryo axis is defined as comprising the plumule, coleoptile, mesocotyl, and at least a portion of the scutellar node of the corn seed. In certain embodiments, the explants comprise an internal moisture content that will not result in germination, and/or the explant is produced from a seed with an internal moisture content at which the seed will not germinate without the application of exogenous moisture. In further embodiments, such an internal moisture content may be from about 3% to about 25% w/w, including about 3, 5, 7, 9, 11, 13, 15, 17, 19, 21, 23, or 25%, and including between about 3% to about 8%, between about 5% to about 10%, between about 6% to about 12%, between about 8% to about 15%, and between about 10% to about 20%. In certain embodiments, the production of explants is automated; and in further embodiments at least a first explant is produced by grinding of the surface of a corn seed.

In another aspect, the invention provides a purified population of dry corn seed explants competent for genetic transformation as described, but further wherein the explants are produced from immature corn seeds. In particular embodiments, such explants may be produced by obtaining an immature corn seed and dehydrating the seed followed by production of an explant as described herein, such as in the case of an explant comprised of the apical portion of the embryo axis of the seed lacking the radical; wherein remaining portions of the corn seed have been substantially removed. In specific embodiments, the dehydrating or drying may result in a seed and/or explant comprising an internal moisture content as described herein.

In still another aspect, the invention provides a method of producing a dry mature corn seed explant, comprising substantially removing the portions of a mature corn seed other than the apical portion of the embryo axis of the seed lacking the radical; and wherein said explant is competent for genetic transformation. In specific embodiments of the method, the apical portion of the embryo axis comprises the plumule, coleoptile, mesocotyl, and at least a portion of the scutellar node of the corn seed. In another embodiment of the invention, tissue is removed from the seed manually. In one example, manual removal of seed portions is carried out by grinding. The explant may also be prepared in an automated process. In further embodiments, the explant may be produced from a seed having, and/or may comprise, an internal moisture content from about 3% to about 25%, including about 3, 5, 7, 9, 11, 13, 15, 17, 19, 21, 23, or 25%, and including between about 3% and about 8%, between about 5% to about 10%, between about 6% to about 12%, between about 8% to about 15%, and between about 10% to about 20%. In still further embodiments, the explant is defined as comprising a size between about 1.5 $mm^2$ to 3.25 $mm^2$, including from about 1.5 $mm^2$ to 2.25 $mm^2$, from about 2.25 $mm^2$ to 2.75 $mm^2$, from about 2.75 $mm^2$ to 3.25 $mm^2$, from about 1.5 $mm^2$ to 2.75 $mm^2$, and from about 2.25 $mm^2$ to about 3.25 $mm^2$, including all exact values included within each of these ranges.

In yet another aspect, the invention provides a method of producing a transgenic corn plant comprising transforming a corn seed explant of the invention with a heterologous DNA. In accordance with the invention the explant may be regenerated into a transgenic corn plant. In one embodiment, *Agrobacterium*-mediated or microprojectile bombardment transformation may be used for transformation of the explant. In such aspects, it is contemplated that transformation is carried under conditions where plant cells are capable of taking up transforming DNA, which may then be integrated into the genome of the plant cell. In this methodology, the cell and/or transforming DNA may or may not be treated to facilitate the uptake and/or integration of the DNA in the chromosome. In yet another embodiment, an explant is transformed with heterologous DNA comprising a selectable marker. In specific embodiments, the selectable marker confers tolerance to a selective agent selected from the group consisting of glyphosate, streptomycin, bialaphos, glufosinate, quizalofop dicamba, 2,4-D, spectinomycin paromomycin, geneticin, and kanamycin. In a particular other embodiment, the method comprises culturing the explant before transformation to induce callus formation, for example, from about 0 hours to about 112 days, including about 0, 2, 4, 6, 8, 10, 12, 14, 16, 18, 20, 22, or 24 hours, 1, 2, 3, 4, 5, 6, 7, 14, 21, or 28 days, or 1, 2, 3, or 4 months. Further embodiments provide for transformation of the explant within about 2 hours of first contacting the explant with an aqueous solution. In still further embodiments, a corn seed explant transformed according to the invention comprises a size between about 1.5 $mm^2$ to 3.25 $mm^2$, including from about 1.5 $mm^2$ to 2.25 $mm^2$, from about 2.25 $mm^2$ to 2.75 $mm^2$, from about 2.75 $mm^2$ to 3.25 $mm^2$, from about 1.5 $mm^2$ to 2.75 $mm^2$, and from about 2.25 $mm^2$ to about 3.25 $mm^2$, including all exact values included within each of these ranges.

In another embodiment, transformation of an explant of the invention is carried out without generating a callus from the explant. Other embodiments involve decontamination of the explant prior to transformation, and culture of the explant to produce multiple buds after transformation. The explant may also be hydrated for about 0.5 to about 4 hours prior to transformation, including about 0.5, 1, 2, 3, or 4 hours. An alternate embodiment provides contacting the explant with KOH prior to transformation. In still another embodiment, the explant is stored for from about 1 hour to about 2 years prior to transformation, including storage for about 0, 2, 4, 6, 8, 10, 12, 14, 16, 18, 20, 22, or 24 hours, 1, 2, 3, 4, 5, 6, 7, 14, 21, or 28 days, 1, 2, 3, 4, 5, 6, 7, 8, 9, 10, 11, or 12 months, or 1 or 2 years. In specific embodiments, a plurality of corn seed explants are transformed.

The foregoing and other aspects of the invention will become more apparent from the following detailed description.

BRIEF DESCRIPTION OF THE DRAWINGS

The following drawings are part of the present specification and are included to further demonstrate certain aspects of the present invention. The invention may be better understood by reference to the drawings in combination with the detailed description of specific embodiments presented herein.

DETAILED DESCRIPTION OF THE INVENTION

The following is a detailed description of the invention provided to aid those skilled in the art in practicing the present invention. Those of ordinary skill in the art may make modifications and variations in the embodiments described herein without departing from the spirit or scope of the present invention.

Figure 1:
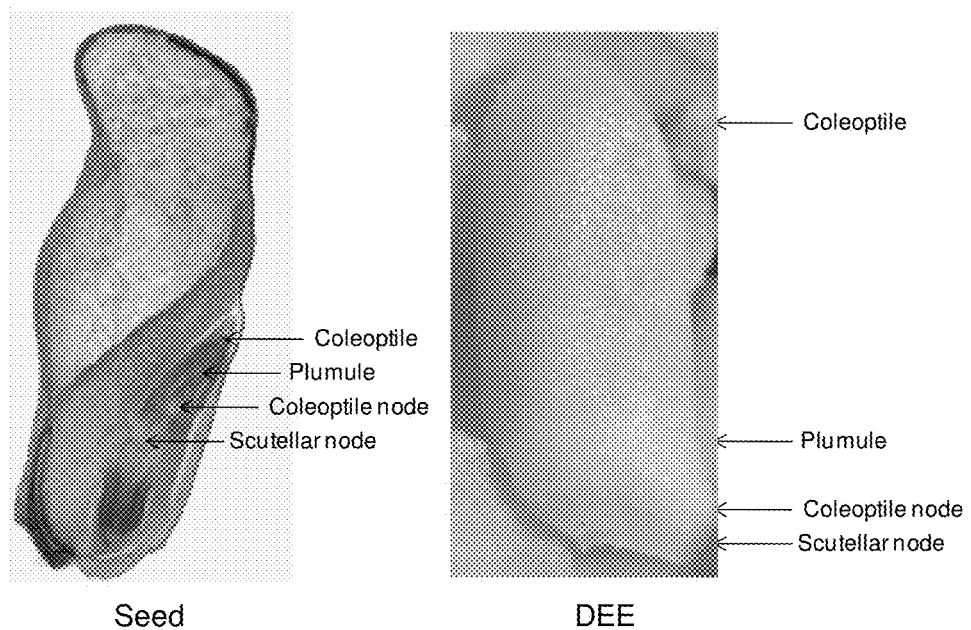
FIG. 1: Shows morphology and anatomy of a corn dry excised explant (DEE).

The current invention provides corn seed explants isolatable from mature corn seeds, referred to herein as dry excised explants (DEEs). Such explants may be produced by removal of seed parts from a mature corn seed to obtain an explant comprising the apical portion of the embryo axis of the seed lacking the radical (FIG. 1). The invention represents a substantial advance in the art, as it eliminates the need for use of explant tissue from immature embryos that has existed to date. Specifically, immature embryo-derived callus transformation systems have been the method of choice for corn transformation since the regeneration of the first transgenic corn plants. However, this system requires the commitment of significant greenhouse space to provide a steady supply of immature embryos in commercial transformation laboratories. In addition, the immature embryo system is genotype-dependent and prone to subtle physiological and environmental variations.

The invention represents a significant advance in that it allows, for the first time, use of dry mature corn seeds for production of a ready supply of plant explant materials and without the genotype limitations inherent in prior transformation systems. Alternate embodiments of this invention provide a purified population of dry immature corn seed explants competent for genetic transformation, for example, produced from dried immature corn seeds in the same manner as dry mature corn seeds. In accordance with the invention, a plurality of DEEs can be produced with a guaranteed stable supply from field-grown mature seeds. This system eliminates the requirement of large greenhouse spaces for explant production and reduces variations associated with the growth of donor plants in the greenhouse and downstream transgenic production. Use of DEEs also avoids the inflexibility in scheduling of immature embryo-based transformation systems, in which initiation of studies is dependent on the successful pollination of donor ear and may require approximately a 2-month waiting period for donor plants to grow.

The DEE explant system described herein allows handling of large amounts of explants in a single study, and is storable, shippable, and is readily amenable to automation. Other variations in explant quality may further be avoided by use of DEEs, such as physiological conditions of immature embryos, the size and stage of immature embryos, and environmental conditions that influence the physiological status of immature embryos, such as ear source, seasons and pest infestation, contribute greatly to the variation in transformation efficiency.

In accordance with the invention centrifugation may be used at one or more steps to obtain transformed explants. For example, centrifugation may find use during inoculation of plant cells with *Agrobacterium* to enhance transformation efficiency.

The transformation of DEE explants is capable of being coupled with use of a multiple bud pathway for efficient generation of transgenic plants and can be used with various desired selection systems. Selectable markers that may be used include, but are in no way limited to, antibiotics, cp4, aadA, and NPT II. The ability to use such a system to obtain stable integration of transgenes into the corn genome and germline transmission of transgenes to the next generation is described herein, confirmed by pollen segregation and F1 & T1 progeny analyses.

The complete transformation process using DEEs was shown to be capable of completion in approximately 9 weeks from initial co-culture to the transplanting of RO plants to soil. The development of such a system avoids the need for use of immature embryos and the associated problems therewith. The implementation of the system vastly reduces risks during the production of transformed plants having valuable new phenotypes, which often requires production of hundreds if not thousands of different transgenic plants to identify just a single commercial transformation event. Program-wide efforts to produce transgenic plants with new traits valuable to farmers can require production of many thousands of transgenic plants in a consistent, quick and cost-effective manner.

The current invention thus advantageously provides large numbers of explants in a steady supply for production of transgenic plants. In specific embodiments of the invention, such explants may be produced and stored prior to transformation. Explant preparation can therefore occur at off-peak times and days, and explants stored for later use, enhancing the efficiency of the overall transformation process. The nature of the explants and their production make this process much more labor efficient and well suited for high volume, high throughput transformation needs. Manipulation of the moisture content of the seed may also be carried out to adjust seed shattering characteristics and subsequent seed and explant vigor and process yield.

The invention further provides in specific embodiments methods and compositions for preparing, selecting and using explants, as well as the explants produced thereby. In certain embodiments, explants according to the invention may be produced manually or in an automated process. For example, seed tissues may be removed from a seed by cutting, grinding, abrasion, or any other similar process. Automated methods for removal of unnecessary seed parts may also be carried out. Fluid, for example, can be used to move explants and separate desirable explants from debris during mechanized handling of seeds, including compressed air, other gases, and liquids. Dry excision of plant embryos to yield transformable explant tissue may be performed, for example, followed by immediate use in transformation methods. Alternatively, dry excised explants may be subsequently stored, with or without treatment prior to storage such as dehydration, for later transformation or other use. Explant preparation and/or storage may thus comprise drying explant and/or seed tissue to obtain a desired hydration level, depending upon the initial moisture content of the seed and/or explant prior to or at the time of excision.

In one embodiment, an explant prepared in accordance with the invention may be defined as having an internal moisture of about 3-30%, including about 3, 4, 5, 6, 7, 8, 9, 10, 11, 12, 13, 14, 15, 16, 17, 18, 19, 20, 21, 22, 23, 24, 25, 26, 27, 28, 29, and 30% internal moisture, and specifically including all ranges derivable between any two such values, and/or may be defined as produced from a mature seed having any such moisture content.

Explants produced in accordance with the invention may be transformed at various times after removal from the mature corn seed and isolation therefrom. In one embodiment, explants are relatively "young" in that they have been removed from seeds for less than a day, for example, from about 1 to 24 hours, such as about 2, 3, 5, 7, 10, 12, 15, 20, or 23 hours prior to use. In other embodiments, explants may be stored for longer periods, including days, weeks, months or even years, depending upon storage conditions used to maintain ultimate explant viability. In other embodiments, explants may be rehydrated prior to transformation, for example, about 1, 2, 4, 6, 12, or 24 hours prior to transformation. Those of skill in the art in particular will understand that storage and/or rehydration times may be optimized such that the quality and/or yield of transformants as well as the efficiency of the transformation process is maximized. This can be carried out for any particular transformation protocol, for example, such as *Agrobacterium*-mediated transformation, microprojectile bombardment transformation, as well as other transformation procedures.

In accordance with the present invention, DEEs may be plated at varying densities in order to optimize transformation frequency. For example, plating DEEs at high density may refer to plating about 75 to about 90 DEEs on a single plate, which may include plating 75, 76, 77, 78, 79, 80, 81, 82, 83, 84, 85, 86, 87, 88, 89, or 90 DEEs on a single plate. Plating DEEs at a mid density may refer to plating about 35 to about 45 DEEs on a single plate, which may include plating 35, 36, 37, 38, 39, 40, 41, 42, 43, 44, or 45 DEEs on a single plate. In addition, plating DEEs at a low density may refer to plating about 25 to about 30 DEEs on a single plate, which may include plating 25, 26, 27, 28, 29, or 30 DEEs on a single plate.

Prior to explant generation, seeds may be subjected to an optional culling step intended to remove seeds with a high degree of bacterial or fungal contamination or seeds that may for any reason be unlikely to produce viable embryonic tissue for use with the present invention. Culling may be carried out, for example, based on parameters such as the size, color, or density of the seed or other physical characteristics that in other contexts would be unobjectionable, and may be adjusted empirically by variation of the excision, sterilization, and storage parameters and by measurement of ultimate yields of viable tissue and of regeneration and transformation efficiencies. Examples of culling methods may include the use of an automatic scale after size sorting. An optical sorter suitable for this purpose is the Sortex Seed Sorter or the Satake ScanMaster™ II (Satake USA Inc., Houston, TX). Other culling techniques may also be employed including culling by moisture content.

In certain embodiments of the invention, explants may be washed prior to use in a fluid, which can be a gas or liquid. An example of use of a gas includes flushing dry explants in sterile air while de-ionizing explants to remove static. Further, specifically charged plates and UV germicidal lamps can be used to remove undesirable particles such as contaminants and microscopic dust. Dry explants may also be subjected to a hydration (pre-culture) to increase internal moisture content prior to being transformed with a heterologous nucleic acid. Transformation is alternatively carried out prior to priming or germination. In this embodiment, seed and/or explant sterilization is carried out, e.g., using Cl gas, followed by breaching of the seed protective outer skin by other means, allowing infiltration of a liquid *Agrobacterium* culture. This process can be carried out immediately following the sterilization and breaching of the seed coat, or after continued storage.

The invention may in particular aspects involve sterilization of explants prior to excision and/or post-excision. Sterilization can include contacting seed or explant material with various fluids (i.e., liquid or gaseous) that serve to reduce or eliminate the presence of viable bacterial or fungal contaminants that could otherwise interfere with seed or embryo viability and later plant tissue culture. Sterilization by application of liquid may also hydrate or partially hydrate the plant tissues, and serve the purpose of priming seeds or embryos. Methods for sterilization include, but are not limited to, the use of chlorine gas, ozone, solutions of bleach or alcohol, ultraviolet light, temperatures of −20° C. or lower, and exposure to a temperature higher than 40° C.

Removal of seed parts to produce an explant in accordance with the invention may be performed manually or by an individual using a variety of mechanical techniques in order to isolate the explant. Seeds may be modified using tools such as forceps or by hand, such as with a grinding tool providing an abrasive force. A seed may be initially fractured followed by manual completion of the explant. Manual fracturing of seed may be accomplished, for example, by striking the seed with a hard object, or by using a press, such as a standard arbor press (e.g., Dayton 4Z328A or Dayton 4Z329D; Dayton Tool Company, Dayton, OH). Some seeds will damaged such as to remove some or all unnecessary portions not to be included in the explant. Selection of the explants having the desired structure can be carried out. As needed, further manual or automated modification may be carried out to obtain the desired explant.

In some embodiments, a dry explant may be first primed, for example, by imbibition of a liquid such as water or a sterilization liquid, and later used for transformation and regeneration. In other embodiments, the seed or the explant may be primed by raising the internal seed moisture content to greater than 30%, holding the seed or the explant at a time point, and then re-initiating imbibition at a later time point.

In an alternative embodiment, the seed or the explant may be primed by raising the internal moisture content to greater than 30%, storing the seed or the explant for a predetermined period, drying the seed or the explant to the internal moisture content of below 20%, and then re-initiating imbibition.

A collection of modified seed material may be screened for suitable explants. For example, a candidate explant may be automatically imaged for analysis of pre-determined quality, such as to test for viability, chemical and biological properties, and suitability in the transformation or regeneration process. Desired explant material may be sorted, for example, by manual sieving, such as a series of geological separation sieves, such that unwanted large and small debris are separated from the desired explant by size exclusion. This could be carried out, for instance with corn material, using U.S. Standard sieves (listed from top to bottom): #16 (1.18 mm opening), and #20 (2.0 mm opening), and then a collection pan on the bottom. Large debris is collected on the #16 sieve, while desired embryo explant material is retained and collected on the #20 sieve. Unwanted fine particles passed through to the collection pan. The explant yield collected on the #20 sieve may be further purified by placing this yield into a vertical airflow separation column (e.g., a MACS-104 machine Seed Tech Systems, LLC., multiple air chamber system, Wilton, CA or an OREGON SEED BLOWER; Hoffman Manufacturing, Jefferson, OR) in which air is passed through the material, blowing lighter unwanted material upward where it is trapped for removal. Modification of the column with various static reduction means would allow for dust removal from embryo surfaces and reduce bio-contamination and remove any unnecessary plant cell and tissue.

Mechanized sieving and airflow separation may also be utilized. For instance, bulk yield from a GP-140 grinder (Modern Process Equipment; Chicago, Illinois) machine that utilizes vibration and gravitational pull to sieve and separate the unwanted seed material from the desired explants. As an example, the Clipper Office Tester or an Eclipse 324 Clipper (Clipper Separation Technologies; A.T. Ferrell Company, Bluffton, IN) may be utilized. This machine has two slots for separation screens to be inserted, whereby seed material is separated according to size. In addition, this machine utilizes a fan that duplicates the function of the previously mentioned vertical airflow separation device, thus giving a final purified yield of explants in a single step.

In one embodiment, a machine for crushing the seeds is conveyed over to a mechanical, density, shape and/or air separator for continuous flow-through of material and for greater automation. The seeds are placed in the machine such as an Apollo roller mill (Sven MFG, Apollo & Products LTD, Saskatoon, SASK), or a 4E grinding mill (Hoffman Manufacturing; Jefferson, Oregon), or a GP-140 grinder (Modern Process Equipment; Chicago, Illinois). Various particle separation devices have been successfully used to isolate useful DEEs, such as: an Eclipse 324 siever, an Indented Cylinder Separator (Westrup Model LA-T fitted with 2.0 mm indent cylinder, Westrup A/S Slagelse, Denmark) and a MACS-104 machine (Seed Tech Systems, LLC., multiple air chamber system, Wilton, CA). This does not represent a complete list of devices that can successfully isolate and recover dry transformable explants from seeds. Using these devices in sequence may be desirable for efficiency and purity of product.

Candidate explant material may be harvested, screened as needed, and selected or subjected to further manual or automated modification. In specific embodiments, one of skill in the art may store explants prepared according to the invention prior to subsequent use. Methods and parameters for drying, storing, and germinating seed are known in the art (e.g., Senaratna et al., 1983, *Pl. Physiol.* 72:620-624, 1983; Vertucci and Roos, 1990, *Pl. Physiol.* 90:1019-1023, 1990; Chai et al., 1998, *Seed Science Research* 8 (Supplement 1):23-28, 1998). Any such conditions may be used as desired, including at temperatures, for example, of from about −80° C. to about 60° C. Temperatures of about −20° C. to room temperature in particular have been found to function well, but the invention is in no way limited to these temperatures.

Various methods have been developed for transferring genes into explant tissue including high velocity microprojection, microinjection, electroporation, direct DNA uptake and, bacterially-mediated transformation. Bacteria known to mediate plant cell transformation include a number of species of the Rhizobiaceae, including, but not limited to, *Agrobacterium* sp., *Sinorhizobium* sp., *Mesorhizobium* sp., and *Bradyrhizobium* sp. (e.g., Broothaerts et al., 2005, *Nature,* 433:629-633, 2005; U.S. Patent Application Publication 2007/0271627). Targets for such transformation have often been undifferentiated callus tissues, although differentiated tissue also has been used for transient and stable plant transformation.

Bacterially-mediated gene delivery (e.g., *Agrobacterium*-mediated; U.S. Pat. Nos. 5,563,055; 5,591,616; 5,693,512; 5,824,877; 5,981,840) can be made into cells, such as corn. The transformed explant or tissues grown therefrom may be cultured in the presence of a selection agent such as the herbicide glyphosate. The result of this step is the termination or at least growth retardation of most of the cells into which the foreign genetic construction has not been delivered and the simultaneous induction of the formation of shoots, which arise from a small cluster of cells including a transformed cell. The transformed tissue can also be cultivated in the presence of other selection agents alone or in combination, including, but not limited to auxin-like herbicides such as dicamba or 2,4-D, MCPA, glufosinate, acetolactate synthase inhibitors, protoporphyrinogen oxidase inhibitors, and hydroxyphenyl-pyruvate-dioxygenase inhibitors, neomycin, kanamycin, paramomycin, G418, aminoglycosides, spectinomycin, streptomycin, hygromycin B, bleomycin, phleomycin, sulfonamides, streptothricin, chloramphenicol, methotrexate, 2-deoxyglucose, betaine aldehyde, S-aminoethyl L-cysteine, 4-methyltryptophan, D-xylose, D-mannose, benzyladenine-N-3-glucuronidase. Examples of various selectable markers and genes providing resistance against them are disclosed in Miki and McHugh, 2004. In one embodiment of the invention a coding region for the selectable marker aminoglycoside adenyltransferase (aadA) conferring resistance to spectinomycin or streptomycin is used (e.g., U.S. Pat. No. 5,217,902; or Sandvang, 1999, *Antimicrob. Agents Chemotherapy* 43:3036-3038).

As is well known in the art, other methods for plant transformation may be utilized, for instance as described by Miki et al., (1993, "Procedures for Introducing Foreign DNA into Plants," in *Methods in Plant Molecular Biology and Biotechnology*, Glick B. R. and Thompson, J. E. Eds., CRC Press, Inc., Boca Raton, pages 67-88), including use of microprojectile bombardment (e.g., U.S. Pat. No. 5,914,451; McCabe et al., 1991, *Bio/Technology* 6:923-926, 1988; U.S. Pat. Nos. 5,015,580; 5,550,318; 5,538,880).

Unmodified and modified protein molecules and their corresponding nucleic acid molecules providing herbicide tolerances to one or more of these herbicides are well known in the art. They are exemplified below and are incorporated herein by reference:

a) sequences encoding tolerance to glyphosate include 5-enolpyruvylshikimate-3-phosphate synthases (EPSPS; U.S. Pat. No. 5,627,061, U.S. Pat. RE39,247, U.S. Pat. Nos. 6,040,497, 5,094,945, WO04074443, and WO04009761), glyphosate oxidoreductase (GOX; U.S. Pat. No. 5,463,175), glyphosate decarboxylase (WO05003362 and U.S. Patent Application 20040177399), and glyphosate-N-acetyl transferase (GAT; U.S. Patent publication 20030083480) conferring tolerance to glyphosate;

b) dicamba monooxygenase (DMO, encoded by ddmC) conferring tolerance to auxin-like herbicides such as dicamba (U.S. Patent Applications 20030115626, 20030135879; Wang et al., 1996; Herman et al., 2005);

c) phosphinothricin acetyltransferase (bar) conferring tolerance to phosphinothricin or glufosinate (U.S. Pat. Nos. 5,646,024; 5,561,236; EP 275,957; U.S. Pat. Nos. 5,276,268; 5,637,489; 5,273,894);

d) 2,2-dichloropropionic acid dehalogenase conferring tolerance to 2,2-dichloropropionic acid (Dalapon) (WO9927116);

e) acetohydroxyacid synthase or acetolactate synthase conferring tolerance to acetolactate synthase inhibitors such as sulfonylurea, imidazolinone, triazolopyrimidine, pyrimidyloxybenzoates and phthalide (U.S. Pat. Nos. 6,225,105; 5,767,366; 4,761,373; 5,633,437; 6,613,963; 5,013,659; 5,141,870; 5,378,824; 5,605,011);

f) haloarylnitrilase (Bxn) for conferring tolerance to bromoxynil (WO8704181A1; U.S. Pat. No. 4,810,648; WO8900193A);

g) modified acetyl-coenzyme A carboxylase for conferring tolerance to cyclohexanedione (sethoxydim) and aryloxyphenoxypropionate (haloxyfop) (U.S. Pat. No. 6,414,222);

h) dihydropteroate synthase (sulI) for conferring tolerance to sulfonamide herbicides (U.S. Pat. Nos. 5,597,717; 5,633,444; 5,719,046);

i) 32 kD photosystem II polypeptide (psbA) for conferring tolerance to triazine herbicides (Hirschberg et al., 1983);

j) anthranilate synthase for conferring tolerance to 5-methyltryptophan (U.S. Pat. No. 4,581,847);

k) dihydrodipicolinic acid synthase (dapA) for conferring to tolerance to aminoethyl cysteine (WO8911789);

l) phytoene desaturase (crtI) for conferring tolerance to pyridazinone herbicides such as norflurazon (JP06343473);

m) hydroxy-phenyl pyruvate dioxygenase for conferring tolerance to cyclopropylisoxazole herbicides such as isoxaflutole (WO 9638567; U.S. Pat. No. 6,268,549);

n) modified protoporphyrinogen oxidase I (protox) for conferring tolerance to protoporphyrinogen oxidase inhibitors (U.S. Pat. No. 5,939,602); and o) aryloxyalkanoate dioxygenase (AAD-1) for conferring tolerance to an herbicide containing an aryloxyalkanoate moiety (WO05107437). Examples of such herbicides include phenoxy auxins (such as 2,4-D and dichlorprop), pyridyloxy auxins (such as fluroxypyr and triclopyr), aryloxyphenoxypropionates (AOPP) acetyl-coenzyme A carboxylase (ACCase) inhibitors (such as haloxyfop, quizalofop, and diclofop), and 5-substituted phenoxyacetate protoporphyrinogen oxidase IX inhibitors (such as pyraflufen and flumiclorac).

A variety of tissue culture media are known that, when supplemented appropriately, support plant tissue growth and development, including formation of mature plants from excised meristems or embryos. These tissue culture media can either be purchased as a commercial preparation or custom prepared and modified by those of skill in the art. Examples of such media include, but are not limited to those described by Murashige and Skoog, (1962, *Physiol Plant* 15:473-497); Chu et al., (1975, *Sci. Sinica* 18:659-668); Linsmaier and Skoog, (1965, *Physiol. Plant.* 18: 100-127, 1965); Uchimiya and Murashige, (1962); Gamborg et al., (1968, *Exp Cell Res.* 50:151-8); Duncan et al., (1985, *Planta* 165:322-332); McCown and Lloyd, (1981, *Combined Proc. Int. Plant Propagator's Soc.,* 30: 421-427); Nitsch and Nitsch, (1969, *Science* 163:85-87); and Schenk and Hildebrandt, (1972, *Can. J. Bot.* 50:199-204), or derivations of these media supplemented accordingly. Those of skill in the art are aware that media and media supplements such as nutrients and growth regulators for use in transformation and regeneration are usually optimized for the particular target crop or variety of interest. Reagents are commercially available and can be purchased from a number of suppliers (see, for example Sigma Chemical Co., St. Louis, MO, and Phytotechnology Laboratories, Shawnee Mission, KS). As used herein, "plant growth regulator" or "plant hormone" refers to compounds that affect plant growth. Plant growth regulators include, but are not limited to, auxins, cytokinins, ABA, gibberellins, ethylene, brassinosteroids, and polyamines. Auxins affect the elongation of shoots and roots at low concentrations but inhibit growth at higher levels. Commonly used auxins include picloram (4-amino-3,5,6-trichloropicolinic acid), 2,4-D (2,4-dichlorophenoxyacetic acid), IAA (indole-3-acetic acid), NAA (α-naphthaleneacetic acid), and dicamba (3,6-dichloroanisic acid). Cytokinins cause cell division, cell differentiation, and shoot differentiation. Commonly used cytokinins include kinetin, BA (6-benzylaminopurine), 2-ip (2-isopentyladenine), BAP (6-benzylaminopurine), thidiazuron (TDZ), zeatin riboside, and zeatin.

The following definitions will aid in the understanding of the description of the invention.

"Callus" refers to a dedifferentiated proliferating mass of cells or tissue.

"Explant" refers to a plant part that is capable of being transformed and subsequently regenerated into a transgenic plant.

"Mature corn seed" refers to a corn seed that has reached full development, normally accompanied by reduction in internal moisture content.

"Tissue culture media" refers to liquid, semi-solid, or solid media used to support plant growth and development in a non-soil environment. Suitable plant tissue culture media is known to one of skill in the art, as discussed in detail subsequently. The media components can be obtained from suppliers other than those identified herein and can be optimized for use by those of skill in the art according to their requirements.

"Nucleic acid" refers to deoxyribonucleic acid (DNA) or ribonucleic acid (RNA).

"Phenotype" refers to a trait exhibited by an organism resulting from the interaction of genotype and environment.

"Recombinant nucleic acid vector" or "vector" refers to any agent such as a plasmid, bacterial artificial chromosome, cosmid, virus, autonomously replicating sequence, phage, or linear or circular single- or double-stranded DNA or RNA nucleotide segment, derived from any source, capable of genomic integration or autonomous replication, typically comprising a nucleic acid molecule in which one or more nucleic acid sequences have been linked in a functionally operative manner. Such recombinant nucleic acid vectors or constructs may be capable of introducing a 5' regulatory sequence or promoter region and a DNA sequence for a selected gene product into a cell in such a manner that the DNA sequence is transcribed into a functional mRNA, which is subsequently translated into a polypeptide or protein.

"Regeneration" refers to the process of growing a plant from a plant cell.

"Regeneration medium" refers to a plant tissue culture medium formulated for regeneration of a transgenic plant and which may contain a selection agent.

"Regenerable callus" refers to callus from which whole plants can be produced.

"Selectable marker" or "screenable marker" refers to a nucleic acid sequence whose expression confers a phenotype facilitating identification of cells containing the nucleic acid sequence.

"Selection" refers to contacting an inoculated explant with a selection medium for obtaining a transformed cell, tissue, or plant.

"Selection medium" refers to a plant tissue culture medium containing a selection agent.

"Substantially removed" in the context of a seed or seed part refers to the removal of most or all of a defined portion in order to yield a transformation-competent explant as described herein.

"Transgenic" refers to organisms into which an exogenous nucleic acid sequence has been integrated.

"Chimeric"" refers to a plant, tissue, explant, or the like, which is composed of two genetically different types of tissue as a result of genetic transformation.

"Transformable explant" refers to any part of a plant that is receptive to transformation.

EXAMPLES

Those of skill in the art will appreciate the many advantages of the methods and compositions provided by the present invention. The following examples are included to demonstrate the preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention. All references cited herein are incorporated herein by reference to the extent that they supplement, explain, provide a background for, or teach methodology, techniques, or compositions employed herein.

Example 1

Plant Materials and Explant Preparation

Agronomically important corn female inbred line DIDA 406 was used in this study to develop a transformation system using mature seed-derived and dry-excised explants (DEEs) through a multiple bud pathway. Dry excised explants (DEEs) were produced through the grinding of surface-sterilized mature corn seeds. DEEs following excision were surface sterilized in 70% ethanol for 4 minutes and rinsed with sterile water 4 times. Sterilized explants were then soaked in sterile water for 1-2 hours and purified through floatation in a plastic container (1.56 L brown sugar canister). Purified explants were treated with 5 mM KOH for 1 hr and then rinsed with Lynx 1595 medium 3 times and subsequently rehydrated in the same Lynx 1595 for 0.5 to 2 hr before inoculation with Agrobacterium. In some studies, purified explants were rehydrated in Lynx 1595 directly without the intermediate step of 5 mM KOH treatment. In some instances, the rehydration medium Lynx 1595 was supplemented with 50 mg/l Nystatin and 10 mg/l TBZ. The Lynx 1595 medium consisted of ⅖ marco salts, ¹⁄₁₀ micro salt and ¹⁄₁₀ vitamins of Gamborg original $B_5$ medium (Gamborg et al., 1968, *Exp Cell Res.* 50:151-8) supplemented with 30 g/l glucose and 3.9 g/l MES. The final pH of the inoculation medium was adjusted to 5.4.

Figure 2:
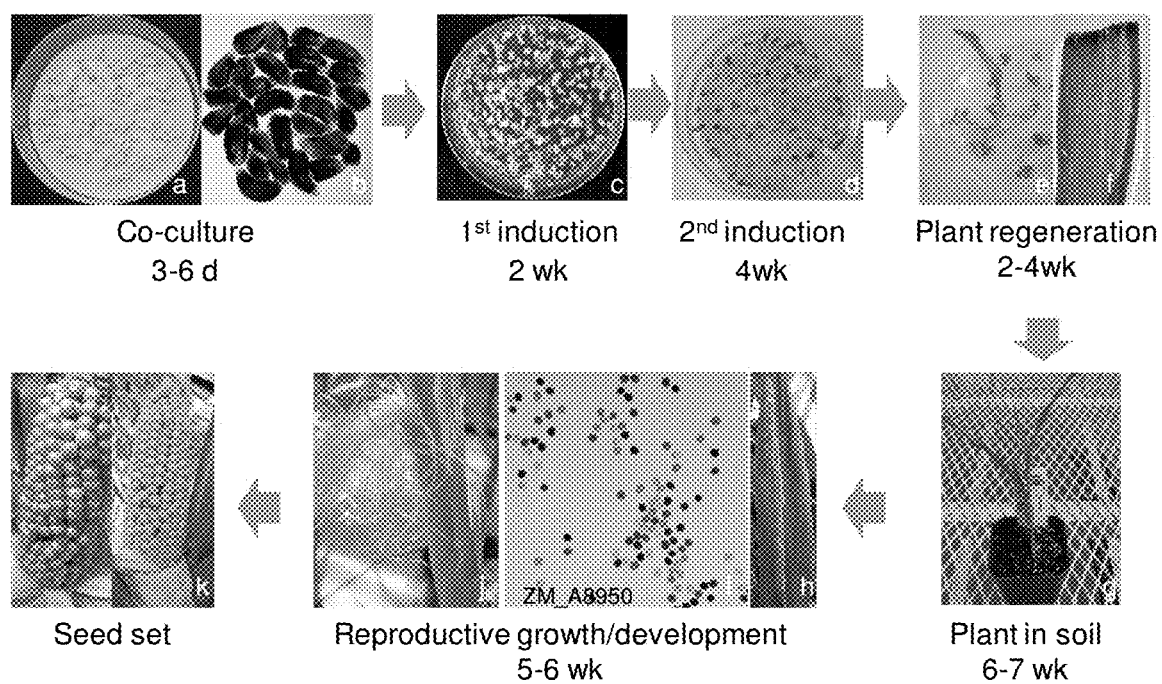
FIGS. 2a-2g: Shows an example of direct transformation of DEEs through a multiple bud pathway.

Fresh DEEs of approximately 1 mm×2 mm after rehydration and KOH treatment in some cases were inoculated with the *Agrobacterium* strain AB32 harboring the appropriate vectors. Following sonication, vacuum infiltration, and centrifugation, inoculated DEEs were co-cultured in a PERCIVAL® incubator at the temperature of 23° C., a relative humidity of 70%, a light density of 90 µmol/m² s and a photoperiod of 16-light and 8-h dark for 3-6 days. After co-culture, explants grew and turned greenish in color (FIG. 2a). Most explants after co-culture had good transient expression (FIG. 2b). The greenish and growing explants were subsequently transferred onto the first bud induction medium and cultured at 28° C., a light density of 60 µmol/m² s, and a photoperiod of 16-light and 8-h dark. After bud induction for a period of two weeks, most explants grew further and became green (FIG. 2c). Green explants were then transferred to the second bud induction medium and cultured at the same conditions as the first bud induction. After a period of approximately four weeks in the second bud induction medium, multiple buds were induced in green explants (FIG. 2d). Green explants with multiple buds were transferred to a plant regeneration medium where shoot regeneration and root differentiation occurred (FIG. 2e). Transgenic plants could be identified by GUS assay of leaf tissue (FIG. 2f). After 2 to 4 weeks of culture, plants with healthy root systems were transplanted to small soil pots (FIG. 2g) for about 1 week for further root development and acclimatization before being transplanted to large pots where the plants entered the reproduction cycle (FIG. 2h, i, j). Tassel and silk formation of transgenic plants occurred approximately 6-7 weeks after transplanting. GUS assay of pollens was used to determine germline transformation. Seeds could be harvested from pollinated ears in 5-6 weeks after pollination (FIG. 2k). Under optimal conditions, the whole transformation process from initial inoculation to transplanting of plants to soil takes about 9 weeks.

Example 2

*Agrobacterium* Inoculation and Co-Culture

*Agrobacterium tumefaciens* strain AB32, derived from the C58 strain (Koncz and Schell 1986, Mol Gen Gent. 204: 383-396) was used in this study. AB32 is a VirG N54D mutant conferring a constitutive expression of VirG and does not require induction signals, such as acetosyringone, for virulence induction. The binary vectors used in this study, pMON 42073, pMON 97367, and pMON 138210 are 1-T vectors. Vector pMON42073 contains four expression cassettes in the following orientation: RBn-uidA-nptII-gfpcp4-LBo. The intron-containing uidA gene (Vancanneyt et al. 1990, *Mol Genet Genomics* 220:245-2503) is driven by a rice actin1 promoter and terminated by the wheat low molecular weight heat shock protein 17 (Hsp17) terminator sequence. The nptII sequence is under the control of a 35S promoter and the nos transcription terminator (Depicker et al. 1982, *J Mol Appl Genet.* 1:561-573). The intron containing gfp cassette is driven by rice actin 1 promoter along with duplicate 35S enhancers plus a rice actin1 intron and terminated by a wheat low molecular weight heat shock protein 17 (Hsp17) terminator sequence. The cp4 gene (Barry et al. 1992, In: Singh B K, Flores H E, Shannon J C (eds) Biosynthesis and molecular regulation of amino acids in plants. American Society of Plant Physiologists, pp 139-145) conferring resistance to glyphosate is driven by the rice actin1 promoter and terminated with the nos transcription terminator.

Figure 3:
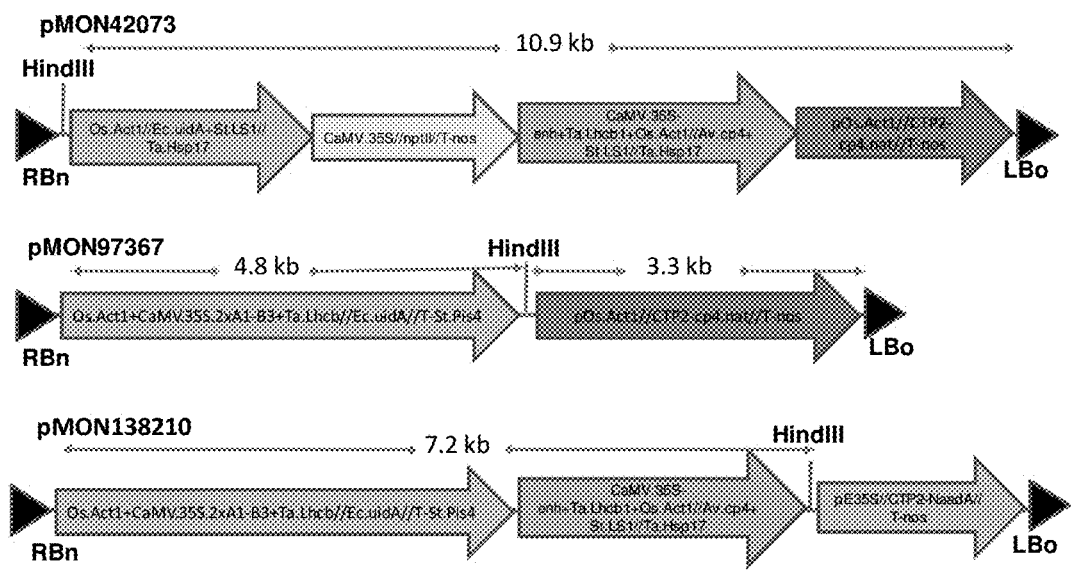
FIG. 3: Shows a schematic description of illustrative T-DNA regions of vectors used in transformation. The expected minimum size of border fragment by Hind III digestion is indicated.

Vector pMON97367 has two expression cassettes in the following orientation: RBn-uid A-cp4-LBo. The same intron-containing uidA gene as in pMON 42703 is driven by the rice actin 1 promoter and duplicated 35S enhancers and terminated with potato proteinase inhibitor II gene signal. The cp4 gene is under control of the rice actin1 promoter and the nos transcription terminator. Vector pMON138210 consists of three expression cassettes in the following orientation: RBn-uidA-gfp-NaadA-LBo. The uidA expression cassette is the same as in pMON 97369. The cp4 expression cassette is the same as in pMON 42073. The monocot codon-optimized chloroplast targeted Ec-aadA sequence (designated as NaadA) is driven by a 35S promoter and rice actin1 intron and terminated by the nos transcription terminator. In all three vectors, the RB region has a 357 bp DNA sequence that was originally isolated from *A. tumefaciens* plasmid pTiT37 (Depicker et al. 1982, *J Mol Appl Genet.* 1:561-573). The LB region has a 456 bp DNA sequence that was originally isolated from *A. tumefaciens* plasmid pTi15955 (Barker et al. 1983, *Plant Mol Biol.* 2:335-350). The RK2 replicon oriV (Cross et al. 1986, *Plasmid* 15:132-146) is used for *Agrobacterium* maintenance and ori-322 for *E. coli* (Huang et al. 2004, *Transgenic Res.* 13:451-461). All the three vectors have an *E. coli* spec (aadA) resistance expression cassette on the backbone for bacterial selection. The schematic representation of the vectors is shown in FIG. 3. All vectors were electroporated into the *Agrobacterium* according to manufacturer's instruction.

For the preparation of *Agrobacterium* inoculum, 500 μL of glycerol stock of *Agrobacterium* was inoculated into a 250 ml LB liquid medium containing 50 mg/l spectinomycin and 30 mg/l gentamycin and cultured on a shaker at 200 rpm at 28° C. for 20-22 hrs. The *Agrobacterium* broth was then centrifuged at 3500 rpm at 4° C. for 25 min. The pellet recovered after centrifugation was resuspended in Lynx 1595 medium and the density was adjusted to 0.3-0.6 at $O.D._{660}$.

For inoculation, floatation-purified and rehydrated DEEs were submerged in 50 ml *Agrobacterium* inoculum in a PLANTCON™ (MP Biomedicals, LLC). The explants were then subjected to sonication in a Honda W-113 ultrasonic Multi-Cleaner at 45 kHZ for 2 min, followed by vacuum infiltration at 25 In Hg for 5 min. The explants were transferred from PLANTCON™ to 50 ml Falcon tube and centrifuged at 291 g for 30 min. In some cases, inoculation was performed without centrifugation. After inoculation, the *Agrobacterium* suspension was removed and explants were transferred to a piece of WHATMAN® #1 filter paper (85 mm) pre-moistened with 1.25-1.50 ml of co-culture media in a 25×100 mm petri dish. In some instances, the co-culture media were supplemented with 0.005% Silwet L77, 50 μM lipoic acid or 50 mg/l Nystatin and 10 mg/l TBZ. Co-culture media used in various experiments and treatments included Lynx 3547, Lynx 1595, Lynx 1595 supplemented with 4 mg/l BAP and 2.2 mg/l picloram, 2-8 mg/l 2,4-D, 10 mg/l IAA, or 10 mg/l NAA. The explants were co-cultured in PERCIVAL® incubators at the temperature of 23° C., a relative humidity of 70%, a light density of 90 μmol/m$^2$ s, and a photoperiod of 16-light and 8-h dark for 3-6 days. After co-culture, samples of explants were taken for GUS transient expression assay.

The various media used for co-culture, 1$^{st}$ bud induction, 2$^{nd}$ bud induction, and plant regeneration are listed in Table 1. Transgenic plants were produced in all four co-culture media summarized in Table 2. The co-culture media included MS (Murashige and Skoog 1962, *Physiol. Plant.* 15: 473-497) based Lynx 3547 and B5 based Lynx 1595. Transformation was successful with Lynx 1595 alone or Lynx 1595 supplemented with 4 mg/l BAP and 2.2 mg/l picloram or 5 mg/l 2,4-D. A two-week delay in selection during the 1$^{st}$ bud induction appeared to have beneficial effects on transformation, particularly with the co-culture medium Lynx 1595 or Lynx 1595 supplemented with 4 mg/l BAP and 2.2 mg/l picloram. For the co-culture medium Lynx 1595 supplemented with 4 mg/l BAP and 2.2 mg/l picloram, the estimated TF was 0.32% for the treatment with a two-week of delay in the 1$^{st}$ bud induction medium. In contrast, the estimated TF was only 0.04% for the treatment without a two-week of delay in selection. Consequently, a two-week delay in selection has been used in subsequent studies.

TABLE 1

Lynx # for the media used in DEE transformation.

| Lynx # | Description |
| --- | --- |
| Lynx 1595 | Two fifth of macro salts, 1/10 micro salts and vitamins of B5 (Gamborg et al. 1968) + 30 g/l glucose + 3.9 g/l MES |
| Lynx 3547 | Lynx 1484 with the addition of 4.0 mg/l BAP + 2.2 mg/l pic + 30 g/l sucrose |
| Lynx 3548 | Lynx 1484 with the addition of 4.0 mg/l BAP + 2.2 mg/l pic + 40 g/l maltose + gly 25 + 200 mg/l carbenicillin + 200 mg/l cefotaxime + 100 mg/l Timentin |
| Lynx 3549 | Lynx 1484 with the addition of 4.0 mg/l BAP + 2.2 mg/l pic + 40g/l maltose + 200 mg/l carbenicillin + 200 mg/l cefotaxime + 100 mg/l Timentin |
| Lynx 3550 | Lynx 2913 with the addition of 1.0 mg/l 2,4-D + 2.2 mg/l pic + gly 25 + 200 mg/l carbenicillin + 200 mg/l cefotaxime + 100 mg/l Timentin |
| Lynx 3551 | Lynx 2913 with the addition of 1.0 mg/l 2,4-D + 2.2 mg/l pic + 30 g/l sucrose + no sel + antibiotics |
| Lynx 3552 | Lynx 1083 with the addition of gly 25 + 200 mg/l carbenicillin + 200 mg/l cefotaxime+ + 100 mg/l Timentin |
| Lynx 3553 | CMSI* with the addition of 2 mg/l BAP and 1 mg/l 2,4-D + gly 25 + 200 mg/l carbenicillin + 200 mg/l cefotaxime + 100 mg/l Timentin |
| Lynx 3554 | CMSI with the addition of 10 mg/l BAP and 1 mg/l 2,4-D + 200 mg/l carbenicillin + 200 mg/l cefotaxime + 100 mg/l Timentin |
| Lynx 3555 | CMSI with the addition of 10 mg/l BAP and 1 mg/l 2,4-D + gly 25 + 200 mg/l carbenicillin + 200 mg/l cefotaxime + 100 mg/l Timentin |
| Lynx 3556 | Lynx 3548 + 25 mg/l meropenem |
| Lynx 3557 | Lynx 3549 + 25 mg/l meropenem |
| Lynx 3558 | Lynx 3550 + 25 mg/l meropenem |
| Lynx 3559 | Lynx 3551 + 25 mg/l meropenem |
| Lynx 3561 | Lynx 3553 + 25 mg/l meropenem |
| Lynx 3562 | Lynx 3554 + 25 mg/l meropenem |
| Lynx 3563 | Lynx 3555 + 25 mg/l meropenem |

*CMSI = MS salts + B5 vitamins + 0.69 g/l proline, 1 g/l casein hydrolysate, 2 g/l MES and 30 g/l sucrose;
gly 25 = 25 μM glyphosate;
pic = picloram.

TABLE 2

Effect of co-culture medium and two week delay in selection at the initial bud induction on transformation frequency.

| Co-culture medium | # of co-cultured DEEs | 1st bud induction medium | 2nd bud induction medium | Plant regeneration medium | # of transgenic plants | Estimated TF (%) |
|---|---|---|---|---|---|---|
| Lynx 1595 | 2,500 | Lynx 3556 (selection) | Lynx 3558 | Lynx 3560 | 2 | 0.08 |
| Lynx 1595 | 2,500 | Lynx 3557 (delay) | Lynx 3558 | Lynx 3560 | 6 | 0.24 |
| Lynx 1595 + 4 mg/l BAP + 2.2 mg/l Pic | 2,500 | Lynx 3556 (selection) | Lynx 3558 | Lynx 3560 | 1 | 0.04 |
| Lynx 1595 + 4 mg/l BAP + 2.2 mg/l Pic | 2,500 | Lynx 3557 (delay) | Lynx 3558 | Lynx 3560 | 8 | 0.32 |
| Lynx 3547 | 2,500 | Lynx 3556 (selection) | Lynx 3558 | Lynx 3560 | 2 | 0.08 |
| Lynx 3547 | 2,500 | Lynx 3557 (delay) | Lynx 3558 | Lynx 3560 | 2 | 0.08 |
| Lynx 1595 + 5 mg/l 2,4-D | 2,500 | Lynx 3563 (selection) | Lynx 3561 | Lynx 3560 | 2 | 0.12 |
| Lynx 1595 + 4 mg/l 2,4-D | 2,500 | Lynx 3562 (delay) | Lynx 3561 | Lynx 3560 | 2 | 0.12 |

Over 140 transgenic plants were produced from more than 10 batches of DEEs processed at different times in over 14 independent experiments and 47 different treatments using selectable marker cp4, aadA, and npt II (Tables 3 and 4). Most of the transgenic plants were derived from cp4 selection, although other markers could be used.

TABLE 3

Regeneration of transgenic plants from three different selectable markers cp4, aadA and npt II.

| Selectable marker | Selective agent | # of DEE batch | # of exp | # of treatment | # transgenic plants |
|---|---|---|---|---|---|
| cp4 | glyphosate | 4 | 4 | 22 | 102 |
| aadA | streptomycin | 3 | 5 | 12 | 26 |
| npt II | paromomycin | 4 | 5 | 13 | 18 |

TABLE 4

Regeneration of transgenic plants from three different selectable markers cp4, aadA and npt II.

| Selectable marker | Construct | # of DEE batch | # of exp | # of treatment | # transgenic plants |
|---|---|---|---|---|---|
| cp4 | pMON 97367 | 4 | 4 | 22 | 102 |
| aadA | pMON 138210 | 3 | 5 | 12 | 26 |
| npt II | pMON 42073 | 2 | 3 | 7 | 8 |
| npt II | pMON 118367 | 2 | 2 | 6 | 10 |
| Total | | 11 | 14 | 47 | 146 |

Example 3

Induction of Multiple Buds and Regeneration of Transgenic Plants

After co-culture, the explants from each co-culture plate were transferred to 5 plates of the initial multiple induction/selection medium-Lynx 3556 (selection medium) or Lynx 3557 (delay medium) and cultured at 28° C., a light density of 60 μmol/m² s and a photoperiod of 16-light and 8-h dark. After initial bud induction/selection for two weeks, growing explants from each plate were subsequently transferred to one plate of the second bud induction medium-Lynx 3558 and cultured at the same condition. In some instances, Lynx 3563 (selection medium) and Lynx 3562 (delay medium) media were used as the initial multiple bud induction medium followed by the use of Lynx 3561 as the second multiple bud induction medium. After the second induction/selection for 4 weeks, surviving explants were transferred to Lynx 3560 for shoot regeneration and root differentiation.

Plants with healthy root systems were regenerated after culture on Lynx 3560 medium for 2-4 weeks. Leaf tissues of the regenerated plants were assayed for GUS expression. Transgenic plants were initially transplanted to a small soil pot and subsequently to a large pot for further development. Leaf tissues were collected for molecular analysis. An example of the corn DEE transformation protocol used is outlined in Examples 1-3 and in Table 5. One of skill in the art will appreciate that the steps and media are illustrative and could be readily modified as desired.

TABLE 5

Corn DEE transformation protocol part I.

| Transformation steps | Protocol |
|---|---|
| Explant purification | 70% ETOH 4 min, floatation purification |
| Explant treatment | 5 mM KOH 1 hr, Lynx 1595 ½ hr, rinse 3× |
| Agro inoculation | Sonication at 45 KHz 2 min, vacuum infiltration 10 min in PLANTCON™, centrifugation at 291 g in 50 ml Falcon tube |
| Co-culture | 1.25-1.5 ml co-culture, a piece of WHATMAN ® # 1 filter paper (8.5 cm), 25 × 100 mm petri dish, unsealed |
| Co-culture condition | 23 C., 70% RH, 90 μmol/m2/s PPFD, 18 h/6 photoperiod |
| Co-culture | Lynx 3547; Lynx 1595 + 4 mg/l BAP & 2.2 mg/l picloram |

TABLE 5-continued

Corn DEE transformation protocol part I.

| Transformation steps | Protocol |
|---|---|
| 1st bud induction | Lynx 3556; Lynx 3557 |
| 2nd bud induction | Lynx 3558 |
| Plant regeneration | Lynx 3560 |

Other working protocols that have generated GUS positive events:

Co-culture media: Lynx 1595, Lynx 1595+2-8 mg/l 2,4-D, 10 mg/l IAA or NAA

The first bud induction medium: Lynx 3562 or Lynx 3563 followed by the second induction medium Lynx 3561

Example 4

Histochemical Assay of GUS Expression

GUS assay for transient and stable transformation was conducted following published protocol (Jefferson 1987, Plant Mol Biol. Rep 5:387-405). DEEs after co-culture for 4-6 d were sampled for transient assay. Leaf tissue from regenerated plants after selection was used to identify transgenic events. Pollens from flowering plants were stained to determine germline transmission. The GUS assay reactions were conducted at 37° C. for a few hours or overnight.

Figure 4:
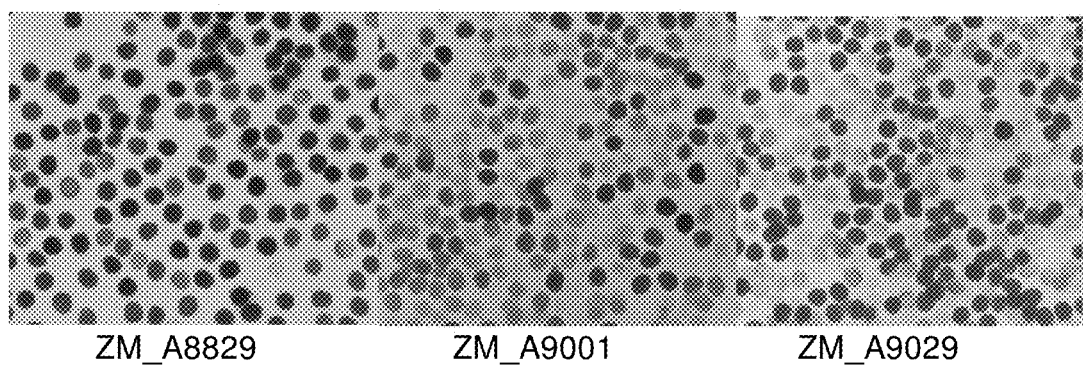
FIG. 4: Shows an example of pollen segregation in transgenic RO plants.

GUS assay of pollens from six events showed that five of them i.e, ZM_A 8829, ZM_A8927, ZM_A8950, ZM_A9001, and ZM_A9029 had clear segregation, which indicated germline transmission of transgenes to progeny (FIG. 4). ZM_A8879 did not have positive GUS staining. That was most likely caused by gene silence due to the presence of >8 copies of uidA gene. GUS assay of T1 progeny between wild type DIDA 406×ZM_A8950 (a single copy event) showed that 28 of 74 plants were GUS positive and 46 were GUS negative. GUS assay of progeny from another 4 copy event showed that 15 out of 29 T1 plants were GUS positive and 14 of them were GUS negative.

Example 5

Southern Blot and Progeny Analyses

Corn DNA exaction was carried out as detailed in the BPD-MQC-Middleton-2711 with one minor modification. Two percent PVP was included in the extraction buffer. DNA was resuspended in 0.1×TE (pH 8.0) buffer and treated with RNAse (10 mg/ml stock) before storage at −20° C. DNA concentrations were determined with a NanoDrop Spectrophotometer. Fifteen to twenty micrograms of DNA were digested overnight at 37° C. in a 100 µL volume with HindIII (NEB) followed by alcohol precipitation and resuspension in 25 µL of milliQ water. Digested DNA from wild-type and transgenic plants was separated on a 1% agarose gel along with the appropriate HindIII digested vector used to generate the transgenic plants. DIG-labeled λ-HindIII digest (Roche) was run alongside the digests. Gels were run overnight at 35 V and processed for Southern blotting according to standard molecular biology protocols. DNA bound to nylon membranes (Hybond-N, GE healthcare) was cross-linked in a UV-Crosslinker (Stratagene) and membranes were probed with the appropriate probes. DIG labeled probes were generated by PCR (PCR DIG-labeling Kit, Roche), and PCR products were gel purified and resuspended in TE buffer. Membranes were hybridized with either uidA and cp4 probes labeled with DIG and washed and probed with anti-DIG antibody conjugated with Alkaline Peroxidase. Following antibody binding, a chemiluminescent AP substrate CSPD (Roche) was added for signal development which was recorded on X-Ray film (Kodak Biomax film). Exposure times were determined by signal intensities.

To determine the frequency of germline events, pollen from flowering was stained. The presence of GUS positive pollen indicates germline transformation. Transgenic plants were either selfed or crossed to wild type DIDA 406. Seedlings derived from T1 or F1 seeds were tested for GUS expression.

Figure 5:
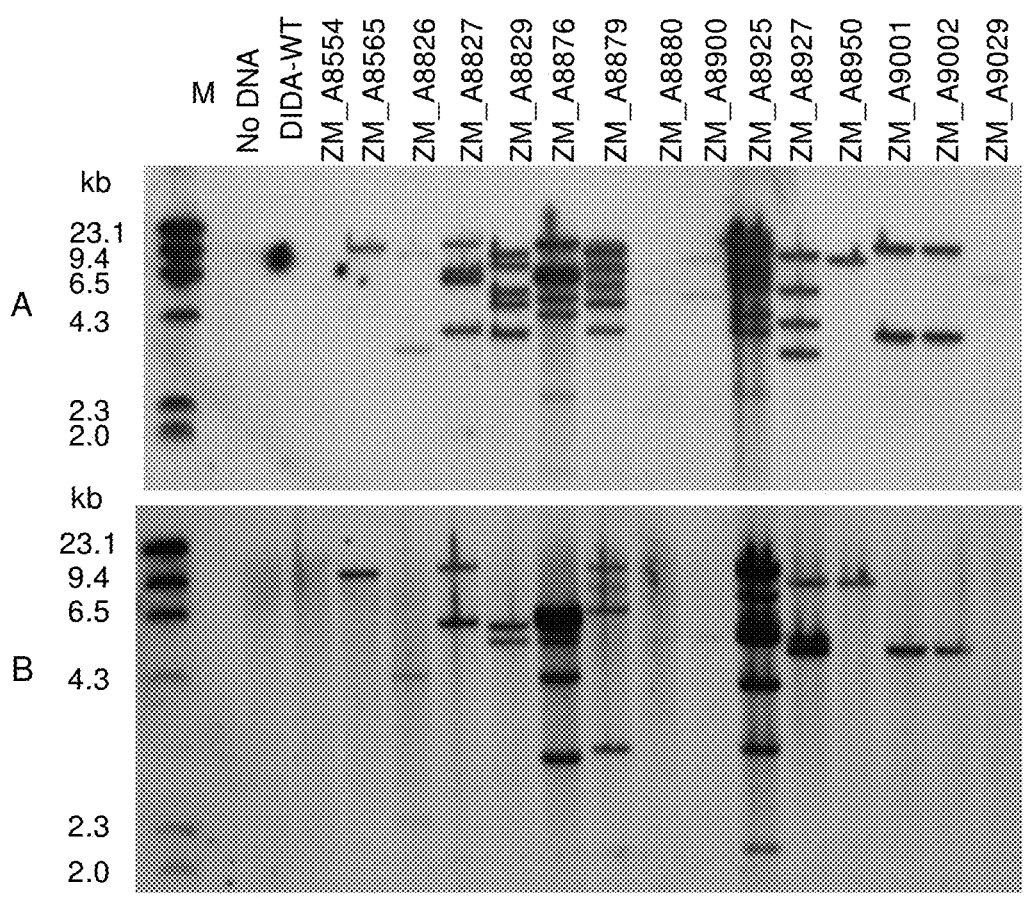
FIGS. 5a-5b: Shows analysis of transgenic plants by Southern blot. A: hybridization with uidA probe; B: hybridization with cp4 probe.
Figure 6:
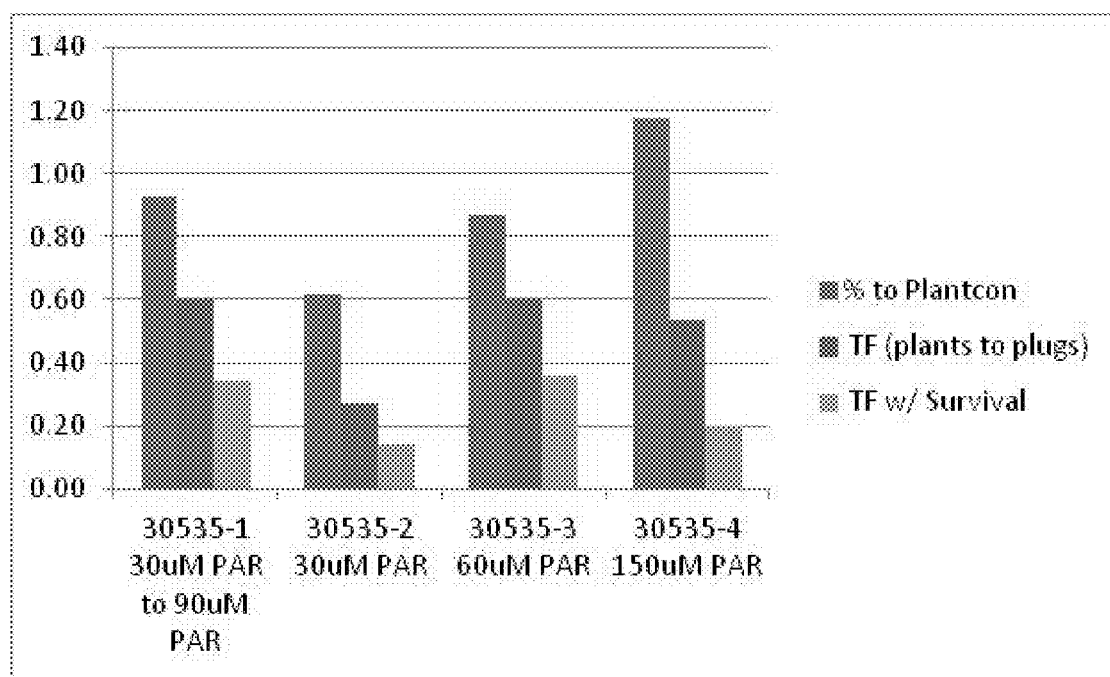
FIG. 6: Shows a graph of the effect of different light intensities. "% to Plantcon" refers to the number of shoots forming in liquid culture moved to Lynx 3647. TF is based on the number of plants moved to horticultural plugs. TF with survival accounts for plants that died in the growth chamber.

Southern analyses were conducted on 15 events derived from three different selectable markers, cp4, aadA and npt II. Events ZM_A8554 and ZM_8565 were transformed by pMON 42073 and selected by paromomycin whereas event ZM_A9029 was transformed by pMON 138210 and selected by resistance to streptomycin. All remaining events were transformed by pMON97367 and selected by resistance to glyphosate. The results of hybridization with uid A probe are shown in the top panel (FIG. 5a) and with cp4 probe presented in the bottom panel (FIG. 5b). As shown in FIG. 5a, ZM_A8565, ZM_A8950 and ZM_A9029 were identified as single copy events. Events ZM_A8826, ZM_A8900, ZM_A9001 and ZM_A9002 had two copies of the uid A gene. All remaining events showed multiple hybridization bands except that ZM_A8554 was an escape. Event ZM_A9001 and ZM_A9002 had similar banding patterns and were considered two subclones. Therefore, approximately 50% events from this set of samples had 1-2 copies of uid A gene. Hybridization with cp4 further confirmed the results for most events transformed by pMON 42073 and pMON 97367. ZM_A8565 and ZM_A8950 were verified as single copy events. However, it is interesting to note that Southern banding pattern with cp4 probe was different from uid A probe for some events. This may indicate partial transfer of T-DNA or T-DNA re-arrangement. Nevertheless, the Southern analyses show that transgenic events from direct transformation of DEE through a multiple bud pathway had stable T-DNA integration into the genome. All these further confirmed germline transmission of transgenes into the next generations.

Example 6

Manual Dry Excision

DEEs can be extracted manually from dry mature corn seed using pliers and similar hand tools. In one example, 100 seeds were hand-excised using pliers yielding 80 embryo-looking particles (80%). Sixteen of them were plated on tissue culture media and incubated to test viability. Four out of these 16 have regenerated in corn plants (25%). Overall, this process was very labor intensive, but resulted in the yield of about 80% of embryos or about 20% of regenerating embryos from seed.

Example 7

Roller Mill Method

DEEs can be recovered from dry mature corn kernels crushed mechanically by passing them through rotating grooved stainless steel rollers. Specifically, dry mature kernels can be passed through the gap between two rollers rotating towards each other. The gap is set to be smaller than the seed size causing rollers to crush kernels. Such crushing can be accomplished using an Apollo roller mill or custom-made prototype roller machine. DEEs are then enriched from the crushed seed by mechanical sieving and may be further enriched by selection. Thus, obtained explants can be intact (containing both whole embryo and scutellum) or partial (shoot portion of the embryo without root portion or scutellum).

In one study, 500 g of mature dry corn kernels were passed through an Apollo roller mill (Sven MFG, Apollo & Products LTD, Saskatoon, SASK) set for 1 mm gap. Resulting crushed material was sieved through standard US mesh screens #16 and #20 to recover DEEs yielding 9.5 g of material containing 80 DEEs/g for the total yield of about 35% from seed.

In another study, 100 seeds were run through the prototype wet roller excisionator 4 times. Twelve explants were hand-recovered (12%). Four were planted on tissue culture media and one of these four regenerated into corn plant (25%). This indicates potential yield of 12% DEEs or 3% regenerable DEEs from seed.

Example 8

Disk Mill and DEE Recovery Method

Efficient kernel crushing for the purpose of DEE recovery could also be accomplished using grinding plates. For example, a mechanical grinder consisting of two round grinding plates with burrs rotating relative to each other at the gap setting smaller than corn kernel and driven by electrical motor was used. The throughput of the crushing process and quality of produced DEEs can be modulated by optimizing of the flow of material through the plates, the gap between plates, burrs used to crush the kernels, and energy applied to the plates and thus to the kernels being crushed. DEEs were recovered from crushed kernels by mechanical sieving. The sieving can be done on a stack of screens that allow size fractionation. Screens are selected so that the top screen retains the largest seed particles and uncrushed seeds, while the bottom screen retains DEEs and DEE-sized particles but allows the smaller particles to pass through. Such sieving can be repeated multiple times for increased efficiency. Yields of up to 59% have been observed. About 80% of DEEs recovered from kernels crushed using grinding plates approach are capable of regeneration of corn plants when placed on appropriate tissue culture media.

In one study, 111.6 kg of dry mature corn kernels were surface sanitized for 10 min with 10% Clorox followed by three rinses with sterile water. This sanitary seed was dried in BryAir Desiccating Dryer (Bry-Air Manufacturing; Sunbury, Ohio) at 100° F. to 7.5% residual moisture level and crushed using 4E grinding mill (Hoffman Manufacturing; Jefferson, Oregon) once and the produced crushed material was sieved using office tester once. This process yielded 1.4 kg of sieved material containing 104 DEEs per gram, producing 31% yield of DEEs from seed. Sample of these DEEs was planted on tissue culture media and allowed to regenerate. 92% of planted DEEs regenerated into corn plants.

In another study, 16.7 kg of dry mature corn kernels were surface sanitized by first exposing them to 70% ethanol for 10 min, rinsed with sterile water, soaked in 10% Clorox, and finally rinsed with sterile water three times and dried in BryAir to 7% moisture level. This dry sanitary seed was crushed by passing it once through custom designed plate grinder and crushed material was sieved using Eclipse 324 siever equipped with 16 and 20 screens (Clipper Separation Technologies; A.T. Ferrell Company, Bluffton, IN). 644.5 g of sieved material was recovered containing 68 DEEs/g for the total yield of 55% from seed. 65% of the recovered DEEs regenerated when plated on tissue culture media.

In yet another study, 200 kg of corn seed was surface sanitized by first flashing it with 70% ethanol, rinsed once with sterile water, soaked for 10 min in 10% Clorox, rinsed three times with sterile water and dried to 8.4% moisture in BryAir. Sanitized seed was crushed using GP-140 grinder (Modern Process Equipment; Chicago, Illinois) and crushed material sieved once on Eclipse 324 siever equipped with standard US mesh screens #16 and #20. 7.4 kg of sieved material was recovered and re-sieved using the same set-up. Following this two-step sieving, 5.3 kg of material was obtained, that contained 70 DEEs/g for the total yield of 44% from seed. To test further enrichment, 285.8 g of this sieved material was run through an indented cylinder (Westrup Model LA-T fitted with 2.0 mm indent cylinder, Westrup A/S Slagelse, Denmark) to produce 153.7 g of enriched material with 107 DEEs/g and total recovery through the indented cylinder step of about 82%.

DEEs recovered from crushed dry mature kernels can also be additionally enriched using other approaches. For example, equipment that takes advantage of air classification has been tested.

In one study, 172.1 g of sieved material containing 63 DEEs/g were applied onto MACS-104 machine (Seed Tech Systems, LLC., multiple air chamber system, Wilton, CA). Most enriched recovered fraction had 42.5 g with DEE content of 127 DEEs/g (or 2 fold purity improvement).

Differential floatation of DEEs and contaminating seed particles has also been noted and can be successfully used for DEE enrichment. In one such example, 1431.7 g of sieved material was floated using sterile water as media. DEEs that floated on the surface of the media were scooped repeatedly until most were collected, while debris, that tend to sink in water, was left behind. Thus enriched DEEs were collected, pooled, and re-dried in laminar flow hood. 50.5 g of dried material was obtained that contained 803 DEEs/g. Thus enriched and re-dried DEEs demonstrated 67% regeneration when planted on appropriate tissue culture media.

Finally, differential optical properties of DEEs and contaminating seed debris can be used to enrich DEEs using visible light. In one study, 12 g of sieved corn material was run through TMCO color sorter (TMCO Inc, Lincoln, Nebraska). After one pass, a fraction of 2.2 g was recovered that was enriched to 176 DEEs/g (2.1 fold enrichment). Rejected fraction could be re-run and the recovered material was pooled with the first fraction totaling 3.53 g at the purity of 156 DEEs/g. As all these approaches to DEE enrichment are all based on different physical properties of the material, they can be combined to produce even more pure material.

Example 9

Internal Seed Moisture Content

Useful DEEs can be produced from seed with different moisture content. In one example, excision of seeds with moisture levels of 7.4% to 22% was tested. Seed was surface sanitized by 70% ethanol treatment followed by rinse with sterile water and 10 min soak in 10% Clorox followed by three sterile water rinses. Sanitized seed was placed in BryAir drier set for 100° F. Samples of seed were taken at different time periods and residual moisture was tested using FOSS analyzer. Seed batches with different measured moisture levels were removed from the drier and excised using either custom-designed grinder or GP-140 grinder. DEEs were recovered by one round of sieving with two screens (US mesh #16 and #20) using office tester. In case of the custom made grinder, DEEs were obtained from all samples, from 7.4% to 22% moisture. Yields from 1% to 40% and purity from 1 to 67 DEEs/g were observed. Optimal moisture level, however, was deemed to be in the range of 7.4% to 10.2%. DEEs produced from seeds in this range regenerated corn plants at an average frequency of 64%.

Example 10

Milling Frozen Corn and Storage of DEEs

The effect of freezing of corn kernels on excision was tested. Mature dry corn kernels were run through the Apollo roller mill immediately after flash-freezing in liquid nitrogen. DEEs were recovered from crushed material by sieving on office tester using standard US mesh screens #10 and #16. DEEs were further enriched by air classification on Oregon Blower. In this trial, 46% yield of DEEs from seed was observed; comparable to non-frozen control. We also have shown that isolated DEEs can be flash-frozen in liquid nitrogen repeatedly without losing the ability to regenerate into corn plants.

In one study, storage of corn DEEs was tested in room temperature, +4° C., −20° C., and −80° C. After 4 months of storage in air-tight containers, no effect of storage on regeneration ability of DEEs has been detected.

Example 11

Corn DEE Transformation—Liquid Culture (LC) Protocol

Explant Preparation: Corn DEEs were stored at −20° C. and removed 30-60 minutes prior to experiment to allow DEEs to come to room temperature. DEEs were placed into a sterile container and surface sterilized for 4 minutes using 70% ethanol with vigorous stirring for 4 minutes. After 4 minutes, DEEs were removed from ethanol using a 3.5-inch stainless steel mesh strainer. Explants were transferred to a new 600-mL beaker, and rinsed 4 times in 400 mL sterile water. Explants were soaked in sterile water for approximately 30 minutes to 1 hour and then transferred to a clean floatation box. Explants were rinsed with reverse-osmosis water. For picked DEEs (partially purified DEEs that are subjected to an additional round of purification), a small floatation box was filled with sterile water approximately ½ inch below the top of the container and the box was shaken horizontally approximately 7-10 times. Once debris settled, purified DEEs were removed with stainless steel mesh skimmer into a new 600-mL sterile beaker. Float-purification was repeated two additional times to recover additional DEEs. Remaining sterile water was removed with a sterile 5-mL pipette and 200 ml Lynx 1595+0.005% Silwet L77 was added to the beaker. Explants were covered and allowed to soak for approximately 1-2 hours prior to inoculation.

Inoculation: A 500-ml Corning centrifuge tube was filled with 150 ml Agrobacterium suspension (OD=0.3-0.35; resuspended in Lynx 1595+0.005% Silwet L77). Explants were removed using a 3.5-inch stainless steel mesh strainer and placed into a tube. Explants were then separated into two different tubes (one with AB32/pMON97367 and the other with construct pMON150110). Centrifuge tubes were placed into a dessicator with caps loosely placed on tubes and vacuum was applied for 5 minutes. Explants floated to the top of the tube after approximately 1-2 minutes of vacuum. Tubes were centrifuged at 655×g for 30 minutes at 4° C. After centrifugation, tubes were swirled to resuspend pelleted Agrobacterium. Explants were poured into a PLANTCON™ lid and Agrobacterium suspension was removed by pipette. The PLANTCON™ lid was tilted to the side, liquid was removed, and any clumps of explants were loosened with pipette to ensure removal of Agrobacterium suspension.

Co-culture: Co-culture plates were prepared by adding 1 ml of Lynx 1595 supplemented with 5 mg/L 2,4-D and 0.005% Silwet L77 to Petri plates (25×100 mm) containing a piece of WHATMAN® #1 filter paper (82 mm). Approximately ½ teaspoon of DEEs were placed onto each co-culture plate and DEEs were spread as evenly as possible, ensuring that all explants were in contact with the filter paper. Petri plates were placed in a 70% humidity-controlled incubator at 23° C. with a light intensity of 90 umol/m$^2$/s (16 hours light/8 hours dark) for 4 days.

Bud Induction: Co-culture plates were removed from incubation and carefully check for contamination prior to starting transfer. Approximately 25-35 DEEs were removed from co-culture plates to felt and filter plates, each containing 10 ml of liquid bud induction media (Lynx 3761). Explants were spread across each plate ensuring that all explants contacted the media and were not on the edge of the plate. Plates were transferred to a light room under light intensity of 90 umol/m$^2$/s (photoperiod of 16 hours light/8 hours dark) at 28° C. for 6-8 days, typically one week. After approximately one week on bud induction media, 6-8 ml (typically 6 ml) of Lynx 3761 were overlaid onto each plate, depending on the response of explants and ensuring that explants were not floating freely in the media. Plates were then returned to the light room under light intensity of 90 umol/m$^2$/s (photoperiod of 16 hours light/8 hours dark) at 28° C. for 6-8 days, typically one week.

Selection and Regeneration: After two weeks on bud induction media, explants were introduced to the selection/regeneration media (Lynx 3763). All remaining Lynx 3761 media was aspirated from each plate and 10 ml of Lynx 3763 was overlaid onto each plate. Plates were again returned to the light room under light intensity of 90 umol/m$^2$/s (photoperiod of 16 hours light/8 hours dark) at 28° C. for 6-8 days, typically one week. After one week on selection/regeneration media, 8-10 ml (typically 8 ml) Lynx 3763 was overlaid to each plate, depending on the response of explants and depletion of media. Plates were maintained visibly wet with a low volume of media without allowing explants to float freely. Plates were again returned to the light room under light intensity of 90 umol/m$^2$/s (photoperiod of 16 hours light/8 hours dark) at 28° C. for 6-8 days, typically one week. 8-10 ml (typically 8 ml) of Lynx 3763 was overlaid to the plates for the subsequent 4 weeks and plates were maintained in the light room under light intensity of 90 umol/m$^2$/s (photoperiod of 16 hours light/8 hours dark) at 28° C. Putative events may appear as early as three weeks into selection/regeneration. Once putative events were approximately one inch, plantlets were transferred into PLANTCON™ containers containing solid media Lynx 3647. Plants were recovered from plates and transferred to PLANTCON™ containers every two weeks. Depending on the experiment, an additional 1-2 overlay steps of 8 ml of Lynx 3763 were done, depending on viability and depletion of media for a particular experiment. Once plants reached the top of the PLANTCON™ and had at least 2-3 well-formed roots, the putative events were transferred to plugs.

Example 12

Corn DEE Transformation—Solid-Liquid Culture (S-LC) Protocol

This Example demonstrates a modified LC method of preparing and culturing explants, in which the liquid bud induction step is replaced with solid media.

Explant Preparation: Corn DEEs were stored at −20° C. and removed 30-60 minutes prior to experiment to allow DEEs to come to room temperature. DEEs were placed into a 1-L sterile container and surface sterilized for 4 minutes using 70% ethanol with vigorous stirring for 4 minutes. Approximately 1000 mL of commercially prepared 70% ethanol were used for sterilizing 10K unpicked (partially purified) DEEs, and approximately 500 mL of commercially prepared 70% ethanol were used for 10K picked DEEs (DEEs subject to an additional round of purification relative to unpicked DEEs). Explants were vigorously stirred for 4 minutes during sterilization. After 3.5 minutes, ethanol was strained off using a 3.5-inch stainless steel mesh strainer for picked DEEs, and a 12-in. sterile stainless steel mesh strainer for unpicked DEEs. Explants were transferred to a new 1-L beaker and rinsed with an equal water volume, stirring for 1 min. Any floating seed coat debris was removed, and liquid was poured off, using stainless steel mesh strainer to catch explants. This process was repeated 3 times with an equal water volume. Explants were transferred to a clean, sterile floatation box. For unpicked DEEs, explants were transferred to a 3-L floatation box (Sterilite) filled to approximately 1 cm below the indent mark with sterile water. After vigorous horizontal shaking, debris was allowed to settle. DEEs were removed into a 1.56-L sterile floatation box. Shake purification was repeated to recover additional purified DEEs. DEEs were added to 200 ml LYNX 1595, ensuring that water was removed prior to adding. Shake purification was repeated twice, and purified DEEs were added to LYNX 1595 with 0.005% Silwet L-77. For picked DEEs, a 1.56-L sterile floatation box was filled with sterile water to approximately ½ in below the top of the container. After vigorous horizontal shaking, debris was allowed to settle and purified DEEs were placed into 200 ml LYNX 1595, ensuring that water was removed prior to adding. Shake purification was repeated twice, and purified DEEs were added to Lynx 1595 with 0.005% Silwet L-77. Explants were covered and allowed to soak for approximately 1-3 hours prior to inoculation.

*Agrobacterium* Preparation (AB32 strain): *Agrobacterium* glycerol stock was obtained from −80° C. storage and thawed at ambient temperature. 100 μL of thawed *Agrobacterium* glycerol stock were used to inoculate 250 ml of LB Liquid media (LYNX 1103) containing appropriate antibiotics for the construct (either 50 mg/L kanamycin or 50 mg/L spectinomycin) and strain (30 mg/L gentamicin for AB32) in a clean, sterile 1 L flask. Cultures were grown in the dark for 21-23 hours at 28° C. with 200 rpm. Prior to pelleting, the $OD_{600}$ of a 1-ml sample of the LB culture was measured to ensured that it was between 0.8 and 1.0. Cultures with $OD_{600}>1.0$ were not used. *Agrobacterium* suspension was pelleted by centrifuging at 5000 rpm at 4° C. for 20 minutes in a 500-mL Oak Ridge centrifuge tube. The pellet was resuspended in 50 ml of LYNX 1595 and the $OD_{600}$ of a $1/20^{th}$ dilution was measured. The concentrated resuspension was diluted to a final $OD_{600}$ of 0.3 in LYNX 1595 prior to inoculation. Just prior to inoculation, 0.005% Silwet L-77 was added to the *Agrobacterium* solution.

Inoculation: LYNX 1595 media was removed and ~50 ml of purified DEEs (equal to starting with 10K) were added to a 500-ml sterile Corning centrifuge tube. Approximately 250 ml of *Agrobacterium* solution ($OD_{600}$=0.3) were added to the bottle, for a total volume of 300-325 ml. If desired, DEEs were vacuum infiltrated by loosening the caps of the centrifuge tubes and placing them in a vacuum chamber with an in-house line (28-30 in Hg) for 5 minutes. DEEs floated to the surface after approximately 2 minutes. The pressure was slowly released to prevent *Agrobacterium* solution from escaping the tube. The tubes were centrifuged at 655×g for 30 minutes at 4° C. After centrifugation, pelleted *Agrobacterium* was resuspended by swirling. *Agrobacterium* solution was removed using a 3.5-in sterile stainless steel hand strainer and tapping onto sterile Ahlstrom or WHATMAN® filter paper.

Co-culture: Co-culture plates were prepared by adding 1 ml of Lynx 1595 supplemented with 5 mg/L 2,4-D and 0.005% Silwet L77 to Petri plates (25×100 mm) containing a piece of WHATMAN® #1 filter paper (82 mm). A level ½-teaspoon of DEEs was placed onto each co-culture plate, with each plate receiving approximately 350-450 purified DEEs. DEEs were spread out as evenly as possible across each co-culture plate ensuring that all explants are in contact with the filter paper. Petri plates were placed in a 70% humidity-controlled incubator at 23° C. with a light intensity of 90 umol/m$^2$/s (16 hours light/8 hours dark) for 4 days.

Bud Induction: Co-culture plates were removed from the incubator and carefully checked for fungal contamination prior to starting transfer. Approximately 25-35 DEEs were removed from co-culture plates to solid bud induction media (LYNX 3676, 25 ml per 20×100 mm plate). To ensure accuracy, a subsample of solid bud induction plates (usually 10-15 per 10K) were counted to ensure a density of between 25-35 DEEs per plate. Plates were gently shaken to spread explants ensure that all explants were in contact with the media. Plates were transferred to a light room under a light intensity of 90 umol/$^{m2}$/s (photoperiod of 16 hours light/8 hours dark, 30-40% Rh) at 28° C. for 14 days.

Selection and Regeneration: After two weeks on bud induction media, explants were bulk transferred to 10 ml liquid selection/regeneration media (LYNX 3763) in a felt/filter plate. For bulk transfer, each bud induction plate was tapped sharply on the side to loosen the DEEs from the media, and responding DEEs were then dumped onto a single felt/filter plate containing 10 ml of LYNX 3763 media. Plates were returned to a light room under light intensity of 90 umol/m$^2$/s (photoperiod of 16 hours light/8 hours dark) at 28° C. for 6-8 days, typically one week. After one week on selection/regeneration media, 8 ml of LYNX 3763 were overlaid onto the plates, ensuring that plates were visibly wet with a low volume of media, but explants were not floating freely. Plates were returned to a light room under light intensity of 90 umol/m$^2$/s (photoperiod of 16 hours light/8 hours dark) at 28° C. for 6-8 days, typically one week. Typically, a Dose-IT media pump was used to overlay media and reduce ergonomic strain. 8 ml of LYNX 3763 were overlaid for the subsequent 4 weeks and plates were maintained in a light room under light intensity of 90 umol/m$^2$/s (photoperiod of 16 hours light/8 hours dark) at 28° C. Putative events may appear as early as three weeks into selection/regeneration, but the first putative events were typically ready for transfer into solid PLANTCON™ containers (LYNX #3647) 4 weeks post-selection. Once putative events were approximately one inch, plantlets were transferred into PLANTCON™ containers containing 100 ml LYNX 3647. Plants were recovered from plates and transferred to PLANTCON™ containers at week 4 post-selection (1st pull) and at week 6 post-selection ($2^{nd}$ pull). Generally, the conversion rate of PLANTCON™ containers to plugs is better when the putative events are one inch or larger. Putative % TF is defined as the # of putative events/# visible DEEs×100. An additional 1-2 overlay steps of 8 ml of LYNX 3763 may also be done, depending on viability and depletion of media for a particular experiment. Putative events were typically plugged after two weeks in PLANTCON™ containers and were not maintained in PLANTCON™ containers for longer than 4 weeks. After two to four weeks in PLANTCON™ containers, the putative events reached the top of the PLANTCON™ containers and had at least 2-3 well formed roots. Histochemical GUS leaf tip staining and striping severity was recorded at time of plugging, according to the following: (a) None; (b) Mild; (c) Mild-margin (white stripe on margin only); (d) Moderate; (e) Severe.

When comparing the Solid-Liquid Culture (S-LC) Protocol with the Liquid Culture (LC) Protocol (Example 11), the S-LC Protocol is advantageous in that it effectively increases the RO event survival by approximately 30%, demonstrating a marked improvement of RO plant quality. The events that are produced using the S-LC Protocol tend to be more vigorous with a larger root system than those produced by the LC protocol, demonstrated by the marked improvement in overall survival between protocols (80% survival for S-LC vs 48% survival for the standard LC protocol).

Example 13

Corn DEE Transformation Using the PAT Gene as a Selectable Marker and Bialaphos as the Selective Agent To screen new selectable markers that may improve transformation frequency (TF) and reduce chimerism for DEE transformation, bialaphos selection experiments were performed to evaluate the DEE response to different levels of bialaphos. DEEs were sterilized using the ethanol method and inoculated with a vector designated pMON131714 (containing PAT and GUS genes in AB32. For inoculation, DEEs were soaked in inoculation medium (LYNX 1595 supplemented with 5 mg/L 2,4-D and 0.005% Silwet) for 2 h, and vacuum-infiltrated for 5 min, followed by centrifugation for 30 min at 600×g. After co-culturing for 4 days, DEEs were cultured on semi-solid medium (#3676) supplemented with 0, 0.5, 1, 2, 3, and 4 mg/L bialaphos, respectively. In two weeks, they were transferred onto plates containing two pieces of felt and 15 ml of liquid regeneration medium containing the same levels of bialaphos or 5 mg/L bialaphos for the DEEs originally on the medium without bialaphos. The regeneration medium was the same as #3763, but glyphosate was replaced with bialaphos. DEEs appeared to have similar growth rates when cultured on the multiple bud induction medium containing different concentrations of bialaphos for approximately two weeks. Although the bialaphos inhibitory effect gradually showed up on the regeneration medium, particularly at 5 mg/L, most of the DEEs already had too much leaf elongation to identify whether any transgenic shoot development occurred. Approximately 30 pieces of growing DEE cultures were assayed for GUS expression after approximately 5 weeks on the regeneration medium, and at least five of them had GUS-positive buds or sectors, although most of them were still very small and covered by elongated leaves. The cultures were transferred onto semi-solid regeneration and root induction medium containing 5 mg/L bialaphos in PHYTATRAY™ containers (Medium 3946) for further growth and selection.

Many shoots gradually died on medium 3946, although some continued to grow and develop roots. A total of 64 resistant plants were moved to a greenhouse and evaluated by histochemical GUS assay. Four GUS-positive plants were identified, all exhibiting normal morphology.

Additional experimentation was done using the same batch of DEEs, and the same construct, but DEEs were cultured on multiple bud induction medium without bialaphos (Lynx 3716) for one week. Ten milliliters of liquid multiple bud induction medium containing 0.5, 1, 3, or 5 mg/L bialaphos were added to each plate to initiate selection. After 2 additional weeks, the DEE cultures were transferred to liquid regeneration medium containing the same level of bialaphos. The cultures responded as described for the previous bialaphos experiment, and therefore were also transferred onto the medium containing 5 mg/L bialaphos (medium 3946) in PHYTATRAY™ containers. One highly resistant plant was identified expressing GUS.

These experiments successfully demonstrated transformation of corn DEEs using the PAT gene as a selectable marker and bialaphos as the selective agent. Plants expressing the GUS gene showed normal morphology.

Example 14

Plating density and cytokinins to improve Corn DEE transformation Experiments were performed to test whether DEE plating density and the use of cytokinins affected corn DEE stable transformation. DEEs were sterilized with 70% ethanol, rinsed, float purified, and then soaked in inoculation media (LYNX 1595 plus 0.005% Silwet L-77) for 1 hour prior to inoculation. For inoculation, the inoculation media was removed from the DEEs and the vector pMON97367 (1T GUS and glyphosate selection cassettes in strain AB32; resuspended in inoculation media LYNX 1595 plus 0.005% Silwet L-77) was added. The Agro:DEE resuspension was vacuum infiltrated for 5 min with house vacuum and subsequently centrifuged at 655×g for 30 minutes at 4° C. DEEs were then co-cultured on Petri plates containing a single piece of WHATMAN® filter paper #1 (82 mm) supplemented with 1 ml LYNX 1595 plus 5 mg/L 2,4-D and 0.005% Silwet L-77 at 70% relative humidity, 23° C. with a 16 hr photoperiod for 4 days. After co-culture for 4 days, DEEs were then transferred to Petri plates containing one filter paper (Ahlstrom) and one felt, plus 10 mls of LYNX 3761 bud induction media for one week at 28° C., 30-40% relative humidity with 16 hr photoperiod at the plating densities (number of DEEs per plate) described in Table 6 below. For the solid bud induction treatment ("S-LC" in Table 6), DEEs were transferred to solid bud induction media LYNX 3676 for two weeks, 30-35 DEEs per plate, in place of the felt/filter matrix with 10 ml of LYNX 3761. For the meta-topolin treatment, meta-topolin replaced the BAP in LYNX 3761 media at the concentration described in the Table 6. After one week, 8 ml of LYNX 3761 or #3761 with meta-topolin replacing BAP as prescribed by treatment was overlaid onto the felt/filter Petri plates and plates were placed back into the 28° C. incubation chamber. After another week, all remaining LYNX 3761 (or 3761 with meta-topolin replacing BAP) media was manually aspirated off and replaced with 10 ml of LYNX 3763 glyphosate selection media. For the "rinse" treatment described in Table 6, the felt/filter matrix was first rinsed by adding 5 ml of sterile water post media aspiration and then aspirating the rinse water off prior to addition of 10 ml of LYNX 3763 media. For the solid bud induction treatment or "S-LC", DEEs were bulk transferred onto a felt/filter matrix containing 10 ml of LYNX 3763 glyphosate selection media. 8 ml of LYNX 3763 was then added every subsequent week to all treatments for six weeks. Developing RO events were removed from the liquid matrix plates as they developed and were rooted in solid LYNX 3647 glyphosate-containing media for 2 to 4 weeks before transferring to soil. As shown in Table 6, decreased plating density of corn DEEs and use of solid bud induction improves the transformation frequency and RO plant quality when used with corn DEE liquid culture.

TABLE 6

Plating Density and Use of Cytokinins in Corn DEE Transformation Liquid Culture

| Treatment Description (French Batch 138, 4 min ethanol) Fast liquid base | # Visible DEEs Treated | # of Events Plugged | Striping Phenotype Frequency (%) | Histo- chemical GUS + from plugging (%) | Stable TF (GUS + events in soil/# visible DEEs × 100) |
|---|---|---|---|---|---|
| CONTROL high density = 75-90 per plate | 2797 | 13 | 10/13 = 77% | 11/13 = 85% | 0.39% |
| Mid density = 35-45 per plate | 3077 | 18 | 14/19 = 74% | 16/19 = 84% | 0.49% |
| Low density = 25-30 per plate | 3077 | 54 | 40/54 = 74% | 47/54 = 87% | 1.5% |
| Meta-topolin 5 mg/L (low density) | 3077 | 42 | 31/42 = 72% | 39/42 = 93% | 1.1% |
| Low density with Bud Induction Rinse | 3077 | 42 | 28/42 = 67% | 34/42 = 81% | 1.1% |
| Solid Bud Induction to Low Density ("S-LC") | 2797 | 35 | 22/36 = 61% | 32/36 = 89% | 1.1% |

Example 15

Light Intensity Effects on Stable Transformation of Corn DEEs

Different light intensities were tested to determine their effect on transgenic plant development and overall TF. Liquid culture was performed (described in Example 11) on 20,000 visible explants of 01DKD2 Batch 127 with no 2,4-D added to the soaking step or to *Agrobacterium* using AB32/pMON97367. The following light intensities were tested (plates were arranged in a single layer to ensure uniform light exposure): (1) 30 μM PAR (bud induction) to 90 μM PAR (selection/regeneration), MYS Standard; (2) 30 μM PAR (bud induction/selection/regeneration); (3) 60 μM PAR (bud induction/selection/regeneration), BPD; (4) 150 μM PAR (bud induction/selection/regeneration).

Conviron carts with ability to adjust light intensity per cart were utilized. A 366813 Quantum Light 3 Sensor Bar was used to measure light intensity. μM is equivalent to μmol/m$^2$ s (the number of photons in units of micromoles striking an area one meter square each second) and PAR stands for Photosynthetically Active Radiation. Lights appeared brighter than original setting and the intensity gradually crept up to ~10 units higher than the original setting, resulting in the need to continually reset carts. Overall, plates seemed to dry out faster for all treatments, particularly Treatment 4. As shown in FOG. 8, plants in Treatment group 4 appeared drier and more stressed from week to week. There was also more shoot proliferation and more browning among plants in this treatment group. A large percentage of putative events that were pulled from liquid culture into PLANTCON™ containers did not develop into plants that were pluggable. The majority of plants turned brown prior to developing into a large enough plant to plug. To determine if these shoots were transgenic, tissue was sampled for histochemical GUS analysis, and the majority of putative events were GUS+. The large majority of plants that were not pluggable were found to be transgenic. % conversion referred to the number of shoots recovered from liquid culture that were able to be transferred to plugs. A pluggable plant is typically defined as one that has a meristem and root structure and has grown to touch the top of the PLANTCON™ container. A relatively high number of plants were recovered from the initial light intensity experiment. For this experiment, plates were placed in a covered sweater box in a single layer to ensure uniform light distribution. The lower light intensity treatment produced the fewest number of plants.

To investigate whether or not stacked plates had a negative effect on recovering plants due to shading of lower plates, differences in TF between plates in a single layer and stacked four high were determined. Conviron carts were lit from above the plates. The construct AB32/pMON97367 was utilized with 30,000 μM DKD2 explants from Batch 137 (unpicked). The following treatments were tested: (1) 30 μM PAR (bud induction) to 90 μM PAR (stacked plates) (BPD); (2) 2-30 μM PAR (bud induction) to 90 μM PAR (single layer plates); (3) 60 μM PAR (stacked plates); (4) 60 μM PAR (single layer plates); (5) 90 μM PAR (stacked plates); (6) 90 μM PAR (single layer plates).

Final TFs indicate a correlation between culturing plates in a single layer and a higher TF. Uniform light distribution may lead to higher TF. In addition, faster evaporation of media (variation in liquid levels) may cause the plates to be drier in the single layer than stacked and thus offer some advantage. Better aeration, increased heat, and more efficient glyphosate selection may also be factors.

It was also useful to understand if uniform or increased light levels for plates are the driving force behind the boost in TF, or if liquid level is a contributing factor. It was observed that there was less liquid remaining in the plates for the single layer treatment each week (particularly noticeable after the 2nd week of selection using Lynx 3763) compared to the stacked treatment.

To determine if liquid levels were a contributing factor, experiments were conducted in a humidity controlled incubator (RH 70%) to help control for evaporation of liquid. Representative plates from both treatments were aspirated to determine how much media needed to be added each week to keep the levels constant. An additional treatment of stacked plates received the BPD volume of media. In addition, 2 other variables were tested in this experiment: (1) 4 min and 2 min ethanol sterilization/treatment. In previous experiments, reduced sterilization duration resulted in more elongation/germination early in the protocol. Another hypothesis of the increased TF in single layer treatments is that glyphosate selection is more efficient due to all the plates getting more light and this may help with the increased germination and growth in the reduced sterilization treatment. (2) Pipette and blot method of *Agrobacterium* removal.

Previous experiments seemed to result in an increased amount of explant death. One hypothesis was that not as much *Agrobacterium* was being removed when using the pipette method, resulting in explant death.

The construct AB32/pMON97367 was utilized with 20K 01DKD2 explants from Batch 141(unpicked). The following treatments were tested: (1) 4 min/pipette/stacked (BPD); (2) 4 min/pipette/stacked (Adjusted Volume); (3) 4 min/pipette/single; (4) 4 min/blot/stacked (BPD); (5) 4 min/blot/stacked (Adjusted Volume); (6) 4 min/blot/single; (7) 2 min/pipette/stacked (BPD); (8) 2 min/pipette/stacked (Adjusted Volume); (9) 2 min/pipette/single. Due to the humidity controlled incubator, liquid levels remained relatively consistent between the stacked adjusted volume and single plate treatments. The BPD treatments had higher liquid levels. Putative TF results are shown in Table JMK4.

Putative TFs for this experiment indicate that there is no difference between the treatments, except that the explants with 2-min ethanol sterilization appeared to result in higher TFs overall compared to the 4-min sterilization. This could be due to the apparent sensitivity of the batch of DEEs to ethanol. In other experiments, 4-min ethanol sterilization resulted in almost complete loss of DEE viability post co-culture. For this experiment, such a drastic effect observed, but more loss of DEE viability was observed for treatments with 4-min sterilization compared to 2-min sterilization. When subjected to higher humidity conditions, the previous effect on TF for single plates compared to stacked plates was not observed.

Additional testing was done to verify conditions in previous experiments. The construct AB32/pMON97367 was utilized with 20,000 01DKD2 explants from an unpicked batch of Chilean seed. A subset of plates from treatments were aspirated to determine how much media needed to be added each week to keep the levels constant between single and stacked plates. An additional treatment of stacked plates received the BPD media volumes. Additional variables tested in this experiment: (1) Higher Light Intensity: 180 μM PAR; 366813 Quantum Light 3 Sensor Bar used to measure light intensity; PAR (Photosynthetically Active Radiation or PAR light); M=μmol/m² s (the number of photons in units of micromoles striking an area one meter square each second—from user manual); (2) DEE Defrost Time: Experiment initiated 1 hr and 2 days post removal from freezer.

The following treatments were tested: (1) DEE Defrost Time—1 hr, Stacked (BPD); (2) DEE Defrost Time—1 hr, Stacked (Adjusted Volume); (3) DEE Defrost Time—1 hr; Single Plate; (4) DEE Defrost Time—1 hr, Stacked (BPD)—higher light intensity; (5) DEE Defrost Time—1 hr, Single—higher light intensity; (6) DEE Defrost Time—2 days, Stacked (BPD); (7) DEE Defrost Time—2 days, Stacked (Adjusted Volume); (8) DEE Defrost Time—2 days; Single Plate; (9) DEE Defrost Time—2 days, Stacked (BPD)—higher light intensity; (10) DEE Defrost Time—2 days, Single—higher light intensity. Initial results indicate a trend between culturing plates in a single layer and a higher TF. In addition, a high level of germination was observed.

Example 16

Early Glyphosate Application to Reduce Chimerism in Corn DEEs

Experiments were performed to investigate the effects of early glyphosate selection on RO chimerism in corn DEEs. DEEs were sterilized with 70% ethanol, rinsed, and then soaked in inoculation media (LYNX 1595 supplemented with 0, 2, 5, or 10 μM glyphosate plus 0.005% Silwet L-77) for 90 minutes prior to inoculation. For inoculation, the inoculation media was removed from the DEEs and the vector pMON97367 (1T GUS and glyphosate selection cassettes in strain AB32; resuspended in inoculation media LYNX 1595 plus 0.005% Silwet L-77) was added. The Agro:DEE resuspension was subsequently centrifuged at 655×g for 30 minutes at 4° C. *Agrobacterium* was removed and DEEs were then co-cultured on Petri plates containing a single piece of WHATMAN® filter paper #1 (82 mm) with 1 ml of LYNX 1595 supplemented with 0, 2, 5, or 10 μM glyphosate plus 5 mg/L 2,4-D and 0.005% Silwet L-77 at 70% relative humidity, 23° C. with a 16 hr photoperiod for 4 days. This co-culture step is abbreviated as "CC" in Table 7 below. After co-culture for 4 days, DEEs were then transferred to Petri plates containing one filter paper (Ahlstrom) and one felt plus 10 ml of LYNX 3761 bud induction media supplemented with 0, 2, 5, and 10 μM glyphosate for one week at 28° C., 30-40% relative humidity with 16 hr photoperiod. After one week, 8 ml of LYNX 3761 or 3761 with 2, 5, or 10 μM glyphosate as proscribed by treatment was overlaid onto the felt/filter Petri plates and plates were placed back into the 28° C. incubation chamber. After another week, all remaining LYNX 3761 media or aforementioned modified LYNX 3761 media was manually aspirated off and replaced with 10 ml of LYNX 3763 glyphosate selection media. Eight milliliters of LYNX 3763 was then added every subsequent week to all treatments for six weeks. Developing RO events were removed from the liquid matrix plates as they developed and were rooted in solid LYNX 3647 glyphosate-containing media for 2 to 4 weeks before transferring to soil. As shown in Table 7, early application of glyphosate selection increases the percent of non-striped or non-chimeric RO events generated as compared to the standard protocol (Treatment #1) in which glyphosate is applied post bud induction.

TABLE 7

Results of experiments testing effects of glyphosate application.

| Tmt # | Treatment | # to Plug | # GUS+ | # Non-striped at plugging | % of Non-striped events at plugging | TF % to soil | % Histochemical GUS+ TF % | TF % for both Histochemical GUS+ and non-striped at plugging |
|---|---|---|---|---|---|---|---|---|
| 1 | BPD 3000 liquid control | 20 | 19 | 3 | 15% | 1.00% | 0.95% | 0.15% |
| 2* | 2 uM gly in bud induction | 24 | 23 | 9 | 38% | 1.20% | 1.15% | 0.40% |
| 3 | 5 uM gly in bud induction | 43 | 38 | 14 | 33% | 2.15% | 1.90% | 0.60% |
| 4* | 10 uM gly in bud induction | 14 | 13 | 9 | 64% | 0.70% | 0.65% | 0.45% |
| 5 | 2 uM gly in CC, bud induction | 11 | 11 | 2 | 18% | 0.55% | 0.55% | 0.10% |

TABLE 7-continued

Results of experiments testing effects of glyphosate application.

| Tmt # | Treatment | # to Plug | # GUS+ | # Non-striped at plugging | % of Non-striped events at plugging | TF % to soil | % Histochemical GUS+ TF % | TF % for both Histochemical GUS+ and non-striped at plugging |
|---|---|---|---|---|---|---|---|---|
| 6 | 5 uM gly in CC, bud induction | 53 | 51 | 16 | 30% | 2.65% | 2.55% | 0.75% |
| 7 | 10 uM gly in CC, bud induction | 35 | 29 | 18 | 51% | 1.75% | 1.45% | 0.70% |
| 8* | 2 uM gly in 1595, CC, bud induction | 27 | 24 | 8 | 30% | 1.35% | 1.20% | 0.25% |
| 9* | 5 uM gly in 1595, CC, bud induction | 36 | 35 | 7 | 19% | 1.80% | 1.75% | 0.35% |
| 10 | 10 uM gly in 1595, CC, bud induction | 17 | 13 | 8 | 47% | 0.85% | 0.65% | 0.40% |

Example 17

Relationship Between DEE Size and Regeneration and Transformation Efficiency

The relationship between DEE area and regeneration was evaluated, using total particles after DEEs were sorted, and significant differences were found based on total particle size (Table 8). Results indicated that size-sorted DEEs performed differently, and small, damaged DEEs do not perform as well as larger DEEs. This was thought to be due to the breakage point at the mesocotyl base and other damage points that may determine how an explant will respond to a transformation protocol.

TABLE 8

Regeneration and DEE Size

| Area (sq mm) | Visible DEE | Regenerable DEE | % Regeneration |
|---|---|---|---|
| Picked | | | |
| 2.065-2.459 | 17 | 10 | 59% |
| 2.549-2.853 | 30 | 27 | 90% |
| 2.853-3.247 | 33 | 27 | 82% |
| 3.247-3.641 | 23 | 22 | 96% |
| 3.641-4.034 | 9 | 8 | 89% |
| Unpicked | | | |
| 2.065-2.459 | 4 | 2 | 50% |
| 2.549-2.853 | 32 | 27 | 84% |
| 2.853-3.247 | 38 | 34 | 89% |
| 3.247-3.641 | 18 | 14 | 78% |
| 3.641-4.034 | 6 | 5 | 83% |

DEEs of varying sizes ranging from 2.25 $mm^2$ to 2.75 $mm^2$, from 2.75 $mm^2$ to 3.25 $mm^2$, and larger than 3.25 $mm^2$ were studied for effects on stable transformation efficiency. It was found that DEEs in the range of from 1.5 $mm^2$ to 3.25 $mm^2$ exhibited the highest transformation efficiency.

Example 18

Force Assisted *Agrobacterium* Transformation

In terms of *Agrobacterium* transfection, application of force through either positive pressure or high gravity may assist with further automation or provide flexibility to corn DEE transformation processes. Gravity alone plays a much larger role than other factors tested. The transfection efficacy of high positive pressure on corn DEEs was tested. Overnight grown AB32/pMON97367 was used. A French Press cell was filled with 20 ml liquid (either inoculum or LYNX 1595 media). Corn DEEs for this test were not surface sanitized to maximize transfection. A range of pressures were applied to DEEs in the presence of inoculum or LYNX 1595 media, and then DEEs were inoculated for 30 min at 1 g (with the exception of a 654-g control exposed to atmospheric pressure conditions. After co-culture, DEEs were bisected and incubated in X-gluc at room temperature for 6 hrs. A sample of DEEs was also collected for MUG analysis, with the remaining surface plated on felt/filter sandwiches with 10 ml LYNX 3761 media. A significant increase in transfection in the DEEs exposed to high pressure was observed, which was comparable to DEEs exposed to high gravity. A sample of 9 plants were sampled for GUS activity, and 7 tested positive for GUS expression in leaf, demonstrating stable transformation of corn DEEs at 1 g using pressure assisted *Agrobacterium*-mediated transformation (PAAT).

DEEs were surface sanitized with 70% EtOH for 4 minutes, holding the pressure application in the French Press constant at 10,000 psi for 5 minutes. A treatment combining high pressure subsequently with high gravity was performed to test for any synergistic interactions. As described previously, after co-culture, DEEs were bisected and incubated in X-gluc at room temperature for 6 hrs. A sample of DEEs were also taken for MUG analysis, with the remaining surface plated on felt/filter sandwiches with 10 ml LYNX 3761 media. A significant increase in transfection in the DEEs exposed to high pressure was observed, which was comparable to DEEs exposed to high gravity. The MUG test also detected a significant positive interaction between the pressure and gravity Effects.

Example 19

Pressure Effect Interaction with the Gravity Effect Test and Vacuum Infiltration Under Sanitizing and Non-Sanitizing Conditions The Pressure×Gravity interaction test was performed using both DEEs surface-sanitized with 70% EtOH for 4 minutes, and with non-sanitized DEEs, holding the pressure application in the French Press constant for 5 minutes. After co-culture, bisected DEEs show increases in transfection with either high pressure or high gravity applications.

Testing was performed to determine whether a pressure effect could be augmented with vacuum infiltration applied either before or after PAAT (under sanitizing and non-sanitizing conditions). TFs in excess of 2% were again obtained with PAAT using 227 atm (under sanitizing conditions), but a large benefit of vacuum infiltration application (either before or after PAAT) was not observed, although TFs were slightly higher with these combinations.

Media formulations as used herein are provided in Tables 9 through 17.

TABLE 9

Composition of LYNX 1083 media.
LYNX 1083

| IngredientName or Instruction | Amount/value Per Liter | Unit per liter |
|---|---|---|
| Phytagel (Sigma P-8169) | 3 | g |
| TC Water | 500 | ml |
| Autoclave. | | |
| MS Basal Salts (Phytotech M524) | 4.33 | g |
| MS Fromm Vitamins (1000x-1129) | 1 | ml |
| Glucose (Phytotech G386) | 10 | g |
| Maltose (Phytotech M588) | 20 | g |
| Asparagine monohydrate (Sigma A-4284) | 0.15 | g |
| Myo-Inositol (Sigma I-3011) | 0.1 | g |
| Add TC water to bring to this volume | 500 | ml |
| pH with KOH to | 5.8 | |
| Filter sterilize with 0.22 micron unit | | |
| Add to Autoclaved Gelling Agent | | |

TABLE 10

Composition of LYNX 1484 media.
LYNX 1484

| IngredientName or Instruction | Amount/value Per Liter | Unit per liter |
|---|---|---|
| TC Water | 500 | ml |
| Phytagar (Gibco 10695-047) | 7 | g |
| Autoclave. | | |
| MS Basal Salts (Phytotech M524) | 4.33 | g |
| MS Vitamins (100x-1208) | 10 | ml |
| BAP (0 . . . 5 mg/ml-1029) | 2 | ml |
| Maltose (Phytotech M588) | 40 | g |
| Casein Hydrolysate, HY-case SF (Sigma C-9386) | 0.5 | g |
| MES (Fisher BP300-100) | 1.95 | g |
| Add TC water to bring to this volume | 500 | ml |
| pH with KOH to | 5.8 | |
| Filter sterilize with 0.22 micron unit | | |
| Add filtered portion to hot gelling agent, stirring briskly | | |
| Picloram (1 mg/mL-1112) | 2.2 | ml |
| Absorbic Acid (50 mg/ml-1293) | 2 | ml |

TABLE 11

Composition of LYNX 2913 media.
LYNX 2913

| IngredientName or Instruction | Amount/value Per Liter | Unit per liter |
|---|---|---|
| MS Basal Salts, no Nitrogen (Phytotech M531) | 0.78 | g |
| Potassium Sulfate (Sigma P-8541) | 1.64 | g |
| Ammonium Nitrate (Sigma A-7455) | 1.65 | g |
| MS Vitamins (100x-1208) | 10 | ml |
| Thiamine HCl (0.5 mg/ml-1027) | 1 | ml |
| 2,4-D (Phytotech D295, 1 mg/ml) | 0.5 | ml |
| Sucrose (Phytotech S391) | 30 | g |
| Proline (Sigma P-5607) | 1.38 | g |
| Casamino Acids (Difco DF0299-17) | 0.5 | g |
| Bring to Volume with TC water | | |
| pH with KOH to | 5.8 | |
| Gelzan CM (CP Kelco 20008194) | 3 | g |
| Autoclave. | | |
| Picloram (1 mg/mL-1112) | 2.2 | ml |
| Silver Nitrate (2 mg/ml-1219) | 1.7 | ml |

TABLE 12

Composition of LYNX 3560 media.
LYNX 3560

| IngredientName or Instruction | Amount/value Per Liter | Unit per liter |
|---|---|---|
| MS Basal Salts (Phytotech M524) | 4.33 | g |
| MS Fromm Vitamins (1000x-1129) | 1 | ml |
| Dextrose (Fisher D16-3) | 10 | g |
| Maltose (Phytotech M588) | 20 | g |
| Myo-inositol (Sigma I-7508) | 0.1 | g |
| Asparagine monohydrate (Sigma A-4284) | 0.15 | g |
| Dissolve | | |
| Bring to volume with TC water | | |
| pH with KOH to | 5.8 | |
| Agarose, Low EEO (Fisher BP160-500) | 3.5 | g |
| Autoclave. | | |
| Carbenicillin (40 mg/ml-1195) | 5 | ml |
| Cefotaxime (50 mg/ml-1686) | 4 | ml |
| Timentin (100 mg/ml-1585) | 1 | ml |
| Glyphosate (0.5M-1031) | 0.05 | ml |
| Meropenem (10 mg/ml-3035) | 2.5 | ml |

TABLE 13

Composition of LYNX 3647 media.
LYNX 3647

| IngredientName or Instruction | Amount/value Per Liter | Unit per liter |
|---|---|---|
| MS Basal Salts (Phytotech M524) | 4.33 | g |
| B5 Stock (1551) | 10 | ml |
| Sucrose (Phytotech S391) | 30 | g |
| Proline (Sigma P-5607) | 0.69 | g |
| Glycine (1 mg/ml-1868) | 2 | ml |
| MES (Sigma M-8250) | 1 | g |
| Dissolve | | |
| Bring to volume with TC water | | |
| pH with KOH to | 5.8 | |
| Agarose, Low EEO (Fisher BP160-500) | 3.5 | g |
| Autoclave. | | |
| Carbenicillin (40 mg/ml-1195) | 10 | ml |
| Cefotaxime (50 mg/ml-1686) | 4 | ml |
| Timentin (100 mg/ml-1585) | 1 | ml |
| Glyphosate (0.5M-1031) | 0.04 | ml |

TABLE 14

Composition of LYNX 3676 media.
LYNX 3676

| IngredientName or Instruction | Amount/value Per Liter | Unit per liter |
|---|---|---|
| MS Basal Salts (Phytotech M524) | 4.33 | g |
| B5 Stock (1551) | 10 | ml |
| Sucrose (Phytotech S391) | 30 | g |
| Proline (Sigma P-5607) | 0.69 | g |
| Casein Hydrolysate, N-Z-Amine A (Sigma C-7290) | 1 | g |
| Glycine (1 mg/ml-1868) | 2 | ml |
| MES (Sigma M-8250) | 1 | g |
| Dissolve | | |
| Bring to volume with TC water | | |
| pH with KOH to | 5.8 | |
| Agarose, Low EEO (Fisher BP160-500) | 3.5 | g |
| Autoclave. | | |
| 2,4-D (1 mg/ml-2106) | 1 | ml |
| BAP (1 mg/ml-2086) | 10 | ml |
| Carbenicillin (40 mg/ml-1195) | 10 | ml |
| Cefotaxime (50 mg/ml-1686) | 4 | ml |
| Timentin (100 mg/ml-1585) | 1 | ml |

TABLE 15

Composition of LYNX 3716 media.
LYNX 3716

| Ingredient Name or Instruction | Amount/value Per Liter | Unit per liter |
|---|---|---|
| MS Basal Salts (Phytotech M524) | 4.33 | g |
| MS Vitamins (100x-1208) | 10 | ml |
| Maltose (Phytotech M588) | 40 | g |
| Casein Hydrolysate, HY-case SF (Sigma C-9386) | 0.5 | g |
| MES (Fisher BP300-100) | 1.95 | g |
| Dissolve | | |
| Bring to volume with TC water | | |
| pH with KOH to | 5.8 | |
| Agarose, Low EEO (Fisher BP160-500) | 3.5 | g |
| Autoclave. | | |
| Picloram (1 mg/ml-1112) | 2.2 | ml |
| BAP (1 mg/ml-2086) | 4 | ml |
| Ascorbic Acid (50 mg/ml-1293) | 2 | ml |
| Carbenicillin (40 mg/ml-1195) | 12.5 | ml |
| Cefotaxime (50 mg/ml-1686) | 4 | ml |
| Timentin (100 mg/ml-1585) | 5 | ml |

TABLE 16

Composition of LYNX 3761 media.
LYNX 3761

| Ingredient Name or Instruction | Amount/value Per Liter | Unit per liter |
|---|---|---|
| MS Basal Salts (Phytotech M524) | 4.33 | g |
| BS Stock 4 (1551) | 10 | ml |
| Sucrose (Phytotech S391) | 30 | g |
| Proline (Sigma P-5607) | 0.69 | g |
| Casein Hydrolysate, N-Z-Amine A (Sigma C-7290) | 1 | g |
| Glycine (1 mg/ml-1868) | 2 | ml |
| MES (Sigma M-8250) | 1 | g |
| Dissolve | | |
| Bring to volume with TC water | | |
| pH with KOH to | 5.8 | |
| Filter sterilize with 0.22 micron unit | | |
| 2,4-D (1 mg/ml-2106) | 1 | ml |
| BAP (1 mg/ml-2086) | 10 | ml |
| Carbenicillin (250 mg/ml-1032) | 1.6 | ml |
| Cefotaxime (50 mg/ml-1686) | 4 | ml |
| Timentin (100 mg/ml-1585) | 1 | ml |

TABLE 17

Composition of LYNX 3763 media.
LYNX 3763

| Ingredient Name or Instruction | Amount/value Per Liter | Unit per liter |
|---|---|---|
| MS Basal Salts (Phytotech M524) | 4.33 | g |
| BS Stock 4 (1551) | 10 | ml |
| Sucrose (Phytotech S391) | 30 | g |
| Proline (Sigma P-5607) | 0.69 | g |
| Glycine (1 mg/ml-1868) | 2 | ml |
| MES (Sigma M-8250) | 1 | g |
| Dissolve | | |
| Bring to volume with TC water | | |
| pH with KOH to | 5.8 | |
| Filter sterilize with 0.22 micron unit | | |
| Carbenicillin (250 mg/ml-1032) | 1.6 | ml |
| Cefotaxime (50 mg/ml-1686) | 4 | ml |
| Timentin (100 mg/ml-1585) | 1 | ml |
| Glyphosate (0.5M-1031) | 0.04 | ml |

All of the compositions and methods disclosed and claimed herein can be made and executed without undue experimentation in light of the present disclosure. While the compositions and methods of this invention have been described in terms of the foregoing illustrative embodiments, it will be apparent to those of skill in the art that variations, changes, modifications, and alterations may be applied to the composition, methods, and in the steps or in the sequence of steps of the methods described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

What is claimed is:

1. A method of producing a transgenic corn plant comprising
    a) transforming a dry mature corn seed explant with a heterologous DNA,
    b) co-culturing the explant in a co-culture medium for about 3 days to about 6 days, wherein the co-culture medium does not contain a selective agent,
    c) transferring the transformed explant to at least a first bud induction medium, wherein the first bud induction medium comprises at least one cytokinin and at least one auxin, wherein the concentration of cytokinin in the first bud induction medium is from 4 mg/L to 10 mg/L, wherein the concentration of auxin in the first bud induction medium is from 1 mg/L to 2.2 mg/L, and wherein the first bud induction medium does not contain a selective agent,
    d) culturing the transformed explant in the first bud induction medium for at least about 14 days to produce a transformed explant with multiple buds, and
    e) regenerating a transgenic corn plant in a regeneration medium, from the transformed explant with multiple buds, wherein the transgenic corn plant is produced without generating a callus from the transformed explant;
wherein delaying selection by culturing the transformed explant in said first bud induction medium for at least about 14 days results in an increased transformation frequency compared to culturing the transformed explant in a different first bud induction medium that contains a selective agent.

2. The method of claim 1, wherein transforming the explant comprises *Agrobacterium*-mediated or microprojectile bombardment transformation.

3. The method of claim 1, wherein the heterologous DNA comprises a selectable marker.

4. The method of claim 3, wherein the selectable marker confers tolerance to a selective agent selected from the group consisting of glyphosate, streptomycin, bialaphos, glufosinate, quizalofop dicamba, 2,4-D, spectinomycin, paromomycin, geneticin, and kanamycin.

5. The method of claim 1, comprising transforming the explant within about 2 hours of first contacting the explant with an aqueous solution.

6. The method of claim 1, wherein transforming said explant is carried out without generating a callus from the explant.

7. The method of claim 1, comprising decontaminating the explant prior to transforming the explant.

8. The method of claim 1, comprising hydrating the explant for about 0.5 to about 4 hours prior to said transforming.

9. The method of claim 1, comprising contacting the explant with KOH prior to said transforming.

10. The method of claim 1, comprising storing the explant for from about 1 hour to about 2 years prior to said transforming.

11. The method of claim 1, comprising transforming a plurality of explants according to claim 1.

12. The method of claim 1, further comprising obtaining transgenic progeny from the transgenic corn plant regenerated from the explant, wherein the progeny comprise the heterologous DNA.

13. A method of producing a transgenic progeny corn plant comprising obtaining a transgenic corn plant prepared by the method of claim 1 and obtaining transgenic progeny of the transgenic corn plant that comprise the heterologous DNA.

14. The method of claim 1, wherein the explant is comprised of the apical portion of the embryo axis lacking the radical, and wherein remaining portions of the corn seed have been substantially removed from the explant.

15. The method of claim 1, wherein culturing the transformed explant comprises culturing the transformed explant in a first bud induction medium comprising at least one cytokinin and at least one auxin, and a second bud induction medium comprising at least one cytokinin.

16. The method of claim 15, wherein second bud induction medium further comprises at least one auxin.

17. The method of claim 1, wherein the dry mature corn seed explant has an internal moisture content of from about 3% to about 25%.

18. The method of claim 1, wherein the dry mature corn seed explant comprises an internal moisture content at which the explant does not germinate.

19. The method of claim 1, wherein the dry mature corn seed explant is produced from a seed with an internal moisture content at which the seed does not germinate.

20. The method of claim 19, wherein the moisture content of the seed is from about 3% to about 25%.

21. The method of claim 1, wherein the step of transforming comprises application of force by positive pressure of between 227 atm and 10,000 psi (680 atm), or by high gravity of between 600 g and 655 g.

22. The method of claim 1, wherein the step of transforming comprises application of force by positive pressure of between 227 atm and 10,000 psi (680 atm), and by high gravity of between 600 g and 655 g.

23. The method of claim 21, wherein high gravity is applied by centrifugation.

24. The method of claim 21, wherein positive pressure is applied in a French Press cell.

25. The method of claim 15, wherein the at least one cytokinin in the first induction medium is 6-benzylaminopurine (BAP).

26. The method of claim 15, wherein the concentration of the at least one cytokinin in the first bud induction medium is higher than the concentration of the at least one cytokinin in the second bud induction medium.

27. The method of claim 15, wherein the second bud induction medium further comprises a selective agent.

28. The method of claim 1, wherein the regeneration medium does not comprise an auxin or a cytokinin.

29. The method of claim 1, wherein the co-culture medium does not comprise an auxin or a cytokinin.

30. The method of claim 26, wherein the second bud induction medium further comprises a selective agent.

31. The method of claim 15, wherein the co-culture medium does not comprise an auxin or a cytokinin.

32. The method of claim 26, wherein the co-culture medium does not comprise an auxin or a cytokinin.

33. The method of claim 1, wherein the at least one auxin in the first bud induction medium is picloram.

34. The method of claim 1, wherein the co-culture medium comprises at least one cytokinin and at least one auxin.

35. The method of claim 34, wherein the at least one cytokinin in the co-culture medium is 6-benzylaminopurine (BAP), or wherein the at least one auxin in the co-culture medium is picloram.

* * * * *

UNITED STATES PATENT AND TRADEMARK OFFICE
CERTIFICATE OF CORRECTION

PATENT NO. : 11,807,846 B2
APPLICATION NO. : 13/873092
DATED : November 7, 2023
INVENTOR(S) : Yurong Chen et al.

It is certified that error appears in the above-identified patent and that said Letters Patent is hereby corrected as shown below:

On the Title Page

At Item (22), please insert: --Filed: Apr. 29, 2013--

Signed and Sealed this
Thirtieth Day of April, 2024

Katherine Kelly Vidal
*Director of the United States Patent and Trademark Office*